United States Patent
Wan et al.

(10) Patent No.: US 11,524,011 B2
(45) Date of Patent: Dec. 13, 2022

(54) H3K27 DEMETHYLASE INHIBITORS IN PEDIATRIC AND JUVENILE OSTEOPOROSIS

(71) Applicant: THE JOHNS HOPKINS UNIVERSITY, Baltimore, MD (US)

(72) Inventors: Mei Wan, Ellicott City, MD (US); Xu Cao, Ellicott City, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 0 days.

(21) Appl. No.: 16/643,672

(22) PCT Filed: Aug. 29, 2018

(86) PCT No.: PCT/US2018/048465
§ 371 (c)(1),
(2) Date: Mar. 2, 2020

(87) PCT Pub. No.: WO2019/046378
PCT Pub. Date: Mar. 7, 2019

(65) Prior Publication Data
US 2020/0222419 A1    Jul. 16, 2020

Related U.S. Application Data

(60) Provisional application No. 62/553,308, filed on Sep. 1, 2017.

(51) Int. Cl.
*A61K 31/55* (2006.01)
*A61P 19/10* (2006.01)
(52) U.S. Cl.
CPC .............. *A61K 31/55* (2013.01); *A61P 19/10* (2018.01)

(58) Field of Classification Search
CPC ............................... A61K 31/55; A61P 19/10
See application file for complete search history.

(56) References Cited

U.S. PATENT DOCUMENTS

2013/0109751 A1    5/2013   Salvatore
2018/0133211 A1*   5/2018   van Wijnen ......... A61K 31/095

FOREIGN PATENT DOCUMENTS

WO      2012/052391 A1      4/2012
WO      WO2012/052390 A1 *  4/2012

OTHER PUBLICATIONS

Zhang, C., "Overview of pediatric bone problems and related osteoporosis" J. Musculoskelet Neuronal Interact. (2012) vol. 12, No. 3, pp. 174-182.

* cited by examiner

*Primary Examiner* — Timothy R Rozof
(74) *Attorney, Agent, or Firm* — Casimir Jones, SC; Robert A. Goetz

(57) ABSTRACT

The present invention provides methods for manipulating epigenetic factors to treat pediatric or juvenile osteoporosis. Specifically, the present invention provides methods for the application of H3K27 demethylase inhibitors in pediatric or juvenile subjects with osteoporosis. Thus, the present invention provides methods of administration of the H3K27 demethylase inhibitor, GSK-J4, to pediatric or juvenile subjects to effectively inhibit primary and secondary pediatric osteoporosis, especially for long-term glucocorticoid treated patients (juvenile rheumatoid disorders, Crohn's disease, nephrotic syndrome, and Duchenne muscular dystrophy) and patients who have compromised mobility (cerebral palsy, Rett syndrome, Duchenne muscular dystrophy, spina bifida, and spinal muscular atrophy).

6 Claims, 13 Drawing Sheets

Specification includes a Sequence Listing.

H3K27 DEMETHYLASE INHIBITORS IN PEDIATRIC AND JUVENILE OSTEOPOROSIS

CROSS-REFERENCE TO RELATED APPLICATIONS

This application is a 35 U.S.C. § 371 U.S. national entry of International Application PCT/US2018/048465, having an international filing date of Aug. 29, 2018, which claims the benefit of U.S. Provisional Application No. 62/553,308, filed Sep. 1, 2017, the content of each of the aforementioned applications is herein incorporated by reference in their entirety.

REFERENCE TO RELATED APPLICATIONS

This application claims the benefit of U.S. Provisional Patent Application No. 62/553,308, filed on Sep. 1, 2017, which is hereby incorporated by reference for all purposes as if fully set forth herein.

STATEMENT OF GOVERNMENTAL INTEREST

This invention was made with government support under grant no. 2R01DK083350, awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Sep. 1, 2017, is named P14712-01_ST25.txt and is 5,957 bytes in size.

BACKGROUND OF THE INVENTION

Life stages, such as embryonic development, growth during postnatal and pubertal periods, and homeostasis in adults are sequential physiologic phases, each with its own characteristics. The skeleton is a remarkably adaptive organ, the development of which closely reflects the physiological stage. For example, skeletal growth is characterized by a sharp increase during early puberty, and deceleration and eventual cessation during late puberty (Rauch, 2012; Yakar and Isaksson, 2016). As growth in length accelerates, bone mass accrual also increases markedly during childhood and adolescence until peak bone mass is achieved in early adulthood (Farr and Khosla, 2015; Heaney et al., 2000; Rizzoli et al., 2010). Between the onset of puberty and young adulthood, skeletal mass approximately do ubles (Bailey et al., 1999; Riggs et al., 1999). Elongation of long bones during the postnatal period and early puberty is driven primarily by chondrogenesis at the growth plates, resulting from chondrocyte proliferation, hypertrophy, and extracellular matrix secretion (Decker et al., 2014; Kronenberg, 2003; Wang et al., 2015a). This process is followed by the co-invasion of blood vessels, osteoclasts, and mesenchymal progenitor cells (MPCs) that give rise to osteoblasts (Gerber et al., 1999; Ono and Kronenberg, 2015), leading to replacement of the cartilage template at the bottom of the growth plate by an ossified bony component, known as primary spongiosa (Kronenberg, 2003). In late puberty, the decline in growth rate is caused primarily by a decrease in the rate of chondrocyte proliferation in growth plate, known as senescence of the growth plate (Lui et al., 2011; Nilsson and Baron, 2004). At this stage, cells at the primary spongiosa of long bone likely also undergo significant changes to adapt to the much slower bone growth/accrual in adulthood. Vascular endothelial cells that form invaded blood vessels and MPCs that replenish bone-forming osteoblasts are highly proliferative during bone growth, but these cells likely stop proliferating or are replaced by other cell types. It was reported that MPCs isolated from the trabecular rich metaphases at two ends of a long bone have superior proliferative ability than the cells within the cortical-rich diaphysis (Siclari et al., 2013). However, little is known about change in the cells of primary spongiosa and the regulatory mechanisms in the skeleton during the transition from fast to slow growth.

Cellular senescence is a stable proliferative arrest that was implicated initially in aging and tumor suppression (Janzen et al., 2006; Kuilman et al., 2010; van Deursen, 2014). Cellular senescence can be induced by cellular damage or stress, including telomere attrition, DNA damage, activation of oncogenes, and oxidative stress. These cells remain viable and metabolically active, but are refractory to mitogenic stimulation. Senescent cells, differing from other quiescent or terminally differentiated non-dividing cells, exhibit essentially stable cell-cycle arrest through the actions of tumor suppressors such as p16INK4a, retinoblastoma, p53, p21CIP1 or others (Baker et al., 2016; Baker et al., 2011). Other characteristics of senescent cells include increased lysosomal β-galactosidase activity (known as senescence-associated β-galactosidase or SA-βGal), robust secretion of inflammatory cytokines/chemokines (known as senescence-associated secretory phenotype or SASP), and nuclear foci containing DNA damage response proteins or distinctive heterochromatin (known as senescence-associated heterochromatin foci) (Janzen et al., 2006; Lee et al., 2006; Molofsky et al., 2006; Wiley et al., 2016). Recent studies suggest that cellular senescence not only contributes to organismal aging and aging-related diseases/disorders (Baker et al., 2016; Baker et al., 2011) but also plays an important role in embryonic development, tissue repair, wound healing, and protection against tissue fibrosis in physiologic conditions in vivo (Demaria et al., 2014; Muñoz-Espín et al., 2013; Serrano, 2014; Storer et al., 2013; Tominaga, 2015; Triana-Martínez et al., 2016).

Increasing in vivo evidence suggests that the concerted action of local niche signals and dynamic chromatin modifications reinforce stem cell fate decisions (Adam and Fuchs, 2016; Adam et al., 2015; Li et al., 2016). Upon changes in the local niche environment, stem/progenitor cells remodel chromatin to survive in transitional states, before undergoing fate selection. Several post-translational modifications of histones, including methylation, acetylation, phosphorylation and ubiquitination, lead to transcriptional regulation of gene expression in the cells. For example, the polycomb group (PcG) protein enhancer of zeste homologue 2 (Ezh2), the histone lysine demethylase Jmjd3, and the DNA methyltransferase Dnmt1 are important chromatin remodeling factors that regulate the proliferation and differentiation of many types of stem/progenitor cells (Chen et al., 2016; Hemming et al., 2014; Hemming et al., 2016; Jing et al., 2016; Juan et al., 2011; Kamminga et al., 2006; Trowbridge et al., 2009; Tsai et al., 2012; Wei et al., 2011; Ye et al., 2012). Ezh2 is the functional enzymatic component of the polycomb repressive complex 2 (PRC2), which has histone methyltransferase activity and trimethylates primarily histone H3 on lysine 27 (i.e., H3K27me3), a mark of transcriptionally silent chromatin. PRC2 consists of 3 core components: EED, SUZ12 and 1 of the 2 histone H3K27 methyltransferases, Ezh1 or Ezh2. Ezh1, a homolog of Ezh2, plays a complementary but nonredundant roles for Ezh2 in mediating H3K27 methylation and gene repression. Conversely, the methyl groups can be removed from H3K27 by histone demethylases Utx and Jmjd3, which demethylate H3K27me3 to H3K27me2 or H3K27me1 (Liu et al., 2015). Because of the essential role of the PRC2 complex in repressing many genes involved in somatic processes, the H3K27me3 mark is associated with the unique epigenetic state of stem/progenitor cells (Juan et al., 2016). During developmental transitions, histone methyltransferases and demethylases are required to dramatically alter epigenetic and gene expression states to create new cell-specific profiles.

Childhood osteoporosis is typically divided into primary and secondary causes, with osteogenesis imperfecta (OI) representing the prototypical primary osteoporosis of childhood. There is a growing list of secondary pediatric osteoporoses (i.e., osteoporosis caused by underlying diseases and/or their treatment), with most falling into two broad categories: glucocorticoid-treated diseases and the disorders which compromise normal weight-bearing and mobility such as cerebral palsy, Rett syndrome, Duchenne muscular dystrophy, spina bifida, and spinal muscular atrophy. Glucocorticoid-induced osteoporosis is the most common form of secondary osteoporosis. Long-term treatment of glucocorticoids has been widely used in the management of chronic inflammatory childhood illnesses such as rheumatoid disorders, Crohn's disease, nephrotic syndrome as well as rare genetic diseases such as Duchenne muscular dystrophy. Although the use of glucocorticoids have led to improved outcomes and survival rates, it is at the cost of substantial adverse effects on bone. Epidemiological studies have shown an up to 34% prevalence of vertebral fractures in children and youth with long-term glucocorticoid therapy.

Although bisphosphonate therapy is the pharmacological treatment of choice in osteoporosis in children, limited evidence for its use in the secondary pediatric osteoporosis. Moreover, the duration and intensity of treatment remain a concern for long-term safety.

Therefore, there still exists an unmet need for new anabolic mediations that stimulate bone formation are required for the management of pediatric osteoporosis.

SUMMARY OF THE INVENTION

Given the beneficial role of cellular senescence in embryonic development and postnatal tissue repair, the inventors investigated whether senescence might also be involved in the cessation of bone growth/accrual during late puberty. The inventors now show that during late puberty, cells in primary spongiosa of long bone undergo senescence, which is also characterized by loss of expression of nestin, an intermediate filament protein. The inventors also identified that the progression of cellular senescence is a normal programmed process governed by an epigenetic mechanism through Ezh2-H3K27me3. Premature acquired senescence during early puberty by genetic deletion of EZH2 leads to impaired angiogenesis and osteoblastogenesis as well as bone loss in later adult life, whereas and increasing H3K27me3 level in the cells rescues the bone-loss phenotype caused by glucocorticoid treatment during puberty.

In preclinical studies, the compound GSK-J4 (N-[2-(2-Pyridinyl)-6-(1,2,4,5-tetrahydro-3H-3-benzazepin-3-yl)-4-pyrimidinyl]-β-alanine ethyl ester) and its use has been shown to effectively inhibit the growth of childhood cancer diffuse intrinsic pontine glioma, representing a promising therapeutic strategy for pediatric brain tumor.

The inventors now show that GSK-J4, a specific H3K27 demethylase inhibitor, elevated H3K27 methylation, blocked the early onset cellular senescence, and rescued the glucocorticoid-induced growth retardation and bone-loss phenotype.

The studies provided herein demonstrate proof-of-concept for manipulating epigenetic factors to treat pediatric or juvenile osteoporosis and short stature due to growth retardation. Specifically, the present inventive methods provide a new opportunity for the application of the H3K27 demethylase inhibitors in children and young adults with osteoporosis and short stature.

In accordance with an embodiment, the present invention provides a method for the treatment of prevention of pediatric osteoporosis in a subject comprising administering to the pediatric subject an effective amount of one or more H3K27 demethylase inhibitors.

In accordance with an embodiment, the present invention provides a method for the treatment of prevention of juvenile osteoporosis in a subject comprising administering to the juvenile subject an effective amount of one or more H3K27 demethylase inhibitors.

In accordance with an embodiment, the present invention provides a method for the treatment of prevention of pediatric or juvenile short stature in a pediatric or juvenile subject comprising administering to the pediatric or juvenile subject an effective amount of one or more H3K27 demethylase inhibitors.

In accordance with an embodiment, the present invention provides a method for treating or prevention of the cessation of bone/growth or accrual in pediatric or juvenile subject comprising administering to the subject an effective amount of one or more H3K27 demethylase inhibitors to the subject.

In accordance with an embodiment, the present invention provides a method for treating or prevention of the cessation of bone/growth or accrual in a pediatric or juvenile subject comprising increasing expression of Ezh2 expression in the primary spongiosa of the subject.

In accordance with an embodiment, the present invention provides a method for treating or prevention of primary osteoporosis in a pediatric or juvenile subject comprising administering to the subject an effective amount of one or more H3K27 demethylase inhibitors to the subject.

In accordance with an embodiment, the present invention provides a method for treating or prevention of secondary osteoporosis in a pediatric or juvenile subject comprising administering to the subject an effective amount of one or more H3K27 demethylase inhibitors to the subject.

DETAILED DESCRIPTION OF THE INVENTION

Figures 1A, 1B, 1C, 1D, 1E, 1F, 1G:
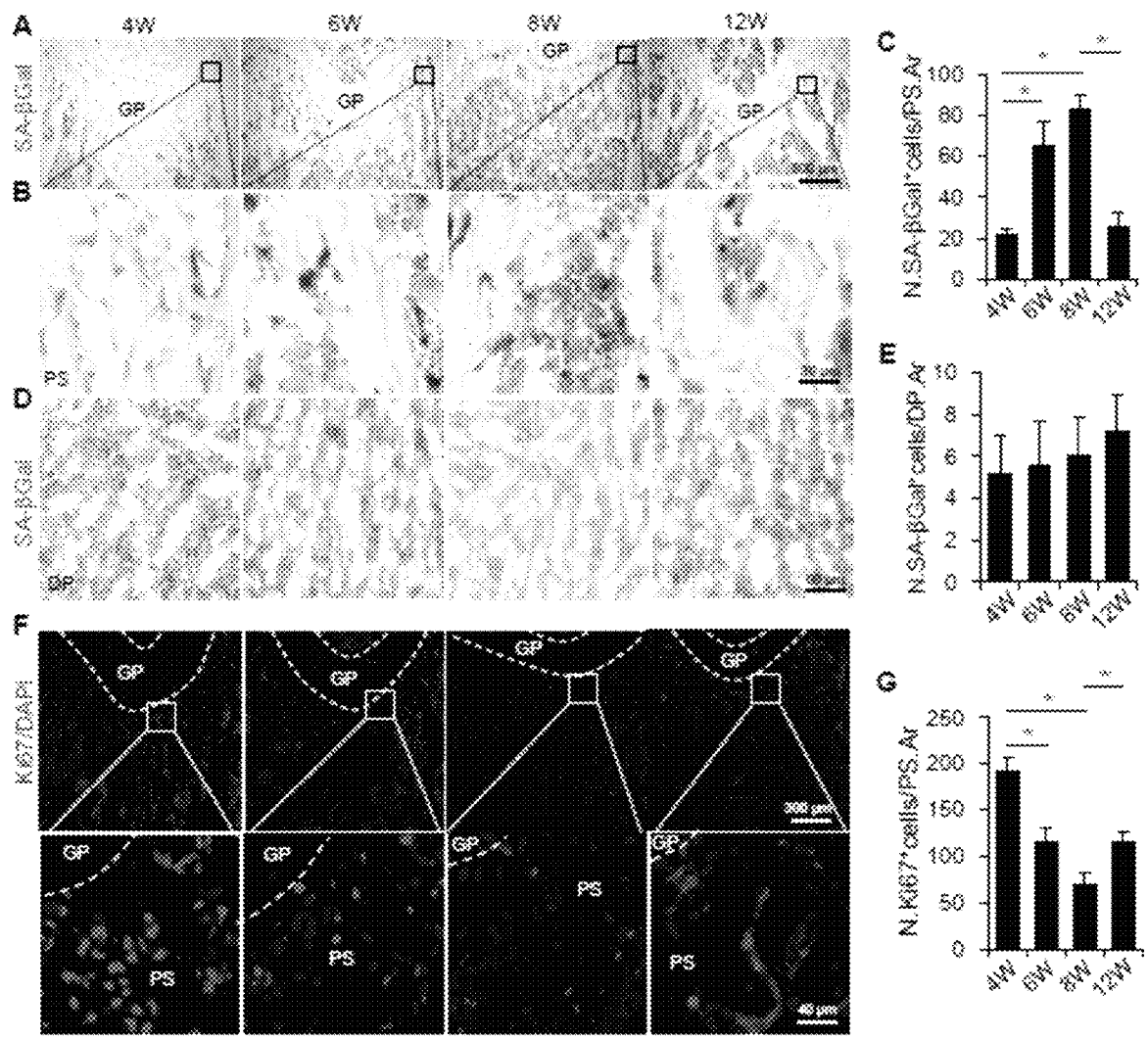
FIGS. 1A-1G. Cellular Senescence Occurs in Primary Spongiosa of Long Bone During Late Puberty. (1A-1E) Representative SA-βGal staining and quantitative analysis of SA-βGal+ cells in femoral metaphysis (1A-1C) and diaphysis (1D, 1E) sections from 4, 6, 8, 12-week-old male mice. Images in (1A) are lower power with boxes outlining the area of higher power in (1B). Numbers of SA-βGal+ cells per mm2 tissue area in primary spongiosa (N. SA-βGal+ cells/PS.Ar) (1C) and diaphysis (N. SA-βGal+ cells/DP.Ar) (1E). (1F-1G) Representative images of immunofluorescence staining (1F) and quantitative analysis of ki67+ (1G) cells in femoral primary spongiosa from 4, 6, 8, 12-week-old male mice. DAPI stains nuclei blue. Images in upper panels in (1F) are lower power with boxes outlining the area of higher power in lower panels. Five mice per group. Data are represented as mean±s.e.m. GP, growth plate. PS, primary spongiosa. *p<0.01 as determined by ANOVA.

In accordance with one or more embodiments, the present invention provides methods for application of epigenetic modifiers at least as part of the therapeutic schema for primary and secondary pediatric osteoporosis with or without short stature, especially for long-term glucocorticoid treated patients (including, for example, juvenile rheumatoid disorders, Crohn's disease, nephrotic syndrome, and Duchenne muscular dystrophy) and patients who have compromised mobility (such as, for example, cerebral palsy, Rett syndrome, Duchenne muscular dystrophy, spina bifida, and spinal muscular atrophy).

The present inventors now show that MPCs in the primary spongiosa of long bones undergo cellular senescence during late puberty when the speed of bone growth/accrual starts to slow. The senescence process is programed and transient as it restricts in a particular region of long bone and follows a specific time course. Cellular senescence was defined by the presence of a senescence marker SA-βGal and a key senescence mediator p16INK4A detected by in situ histology and immunofluorescence staining of the bone tissue sections. Cell senescence was also supported by the reduced proliferation rate, detected by BrdU labeling and immunostaining of the proliferation marker Ki67. Metaphyses, especially the primary spongiosa that lies immediately adjacent to the growth plate, are the zone of active neoangiogenesis and osteogenesis during the rapid postnatal and pubertal skeletal growth periods.

During long bone growth, the whole metaphysis is modeled. The primary spongiosa replaces the cartilage templates, and the secondary spongiosa replaces the primary spongiosa. The volume of secondary spongiosa is stable, but the part distal to the growth plate is resorbed where new secondary spongiosa is formed more proximal to the growth plate.

The present inventors found that cell senescence was barely detectable during early puberty, became obvious during late puberty, and was much reduced in adulthood in the primary spongiosa of mouse femora. There were many fewer senescent cells in the secondary spongiosa relative to the primary spongiosa and almost undetectable in the diaphysis in the center bone marrow area, indicating that the cellular senescence may represent the primary spongiosa involuting during the late puberty.

The present inventors also found that the senescence of the cells was reduced in mice treated with growth hormone (GH) and was accelerated in mice treated with prednisolone, indicating that the progression of this process can be manipulated by external factors known to affect skeletal linear growth. Cellular senescence in primary spongiosa is an important signature for the transition from fast to slow growing phase in long bones.

The present inventors now identify that the gradual loss of nestin expression is another feature of cellular senescence in the primary spongiosa of long bones during late puberty. Nestin is a type IV intermediate filament protein expressed in many progenitor cell types, including neural progenitor cells, progenitors of cardiac, skeletal and smooth muscle, endothelial, hepatic, and pancreatic tissues (Delacour et al., 2004; Kachinsky et al., 1994; Mokrý and Nemecek, 1998; Sun and An, 2004). Given that other intermediate filament proteins are known to be expressed when a cell is dividing, it is logical to postulate that nestin is the preferred intermediate filament for cell division of bone marrow MPCs.

The present inventors identified that most of Nestin-expressing cells at the primary spongiosa of long bones also expressed the proliferation marker Ki67 and were labeled by BrdU, whereas the cellular senescence marker p16INK4A was exclusively expressed in the Nestin-GFP-negative cell population and were unable to be labeled by BrdU.

The present inventors' results suggest that nestin-positive cells in primary spongiosa of long bone proliferate much faster than nestin-negative cells in the same region during periods of rapid bone growth. Because these cells are likely no longer required in this particular region during adulthood, they stop proliferating and undergo senescence during late puberty. Bone marrow nestin+ cells were identified as HSC niche cells containing all bone marrow MSC activity (Méndez-Ferrer et al., 2010). Recent findings revealed that Nestin-GFP and Nestin-Cre labeled a heterogenous population of precursor cells that contain precursors in endothelial and mesenchymal lineage, as well as Schwann precursor cells (Isern et al., 2014; Kusumbe et al., 2016; Ono et al., 2014a).

Consistent with these reports, the present inventors found that in early puberty, there are high percentage of Osx+ osteoprogenitor cells in Nestin-expressing cells in the primary spongiosa region, implicating a high proliferating property of these cells, likely because of a high demand for osteoblast replenishment for bone formation during this period of time. An interesting phenomenon from the present study is that while the number of the Nestin-GFP+ cells gradually lost in the primary spongiosa of long bone during late puberty, LepR+ cells gradually increased in this region. The present data suggests that nestin+ cells in the primary spongiosa of long bones may represent growth-associated progenitor cells, the function of which will be gradually replaced by adult stem/progenitor cells during late puberty.

The present inventors' work establishes the role of Ezh2-H3K27me3 as a key epigenetic regulator that controls the onset and progression of cell senescence during the transition of fast- to slow-growing phase of long bones. qRT-PCR and ChIP analysis suggest that Ezh2 downregulation in Nestin-GFP– MPCs led to increased expression of cyclin dependent kinase inhibitors p16INK4A, p21CIP1, p27KIP1, and p15INK4b by reducing the H3K27me3 marker near the TTSs on their promoter regions. More importantly, in vivo studies using genetic Ezh2 ablation mouse model revealed that removal of the H3K27me3 marker in nestin+ cells in early pubertal mice caused premature cellular senescence in primary spongiosa, reduced vascularization and osteogenesis, mimicking the phenotype of late pubertal bone.

Thus, the present inventors now show that Ezh2-H3K27me3 modulates the senescence of MPCs in a spatiotemporal manner. The self-renewal and proliferative capacity of cells in primary spongiosa of fast-growing bones are maintained by a high level of Ezh2-H3K27me3, whereas loss of Ezh2-H3K27me3 during late puberty leads to cell senescence.

In the present in vivo mouse models, decreasing H3K27me3 by deletion of Ezh2 in the nestin+ cell population resulted in premature cellular senescence in early puberty and reduced osteogenesis. It appears that the primary role of Ezh2 in MPCs is not influencing the lineage commitment/differentiation in this particular location at this specific time period. The discrepant results from our model system and the studies using mesenchymal stromal cells/preosteoblasts are likely attributable to the distinct origin of the cells and microenvironments in which the cells reside.

The present inventors' finding that Ezh2-H3K27me3 regulates the cellular proliferation/senescence in primary spongiosa during skeletal growth/cessation implies another important role of H3K27 methylation in skeleton during this special period of life, i.e. regulating the rates of bone formation and bone mineral accrual to harmonize the speed of bone elongation.

Dysregulations/perturbations during childhood and puberty may lead to skeletal disorders such as primary bone fragility disorders and secondary pediatric osteoporosis caused by chronic diseases and/or their treatment (Mundy et al., 2016; Rizzoli et al., 2010). Peak bone mass in childhood is a major determinant for the incidence of distal forearm fractures in this period. In addition, peak bone mass in childhood is associated with bone mass and fracture risk later in life (Farr and Khosla, 2015). An epidemiologic study demonstrated that 60% of the risk of osteoporosis can be explained by the bone mineral acquired by early adulthood (Cooper and Melton, 1992; Farr and Khosla, 2015; Rosen, 2000; Veldhuis-Vlug and Rosen, 2016) and a 10% increase in peak decreased adult fracture risk by up to 50% (Hernandez et al., 2003).

The present inventors finding that deletion of Ezh2 in nestin+ cells during early puberty increases the risk of osteoporosis in later adulthood suggests that premature cellular senescence in the primary spongiosa region during the prepubertal or early pubertal phase caused by Ezh2-H3K27me3 loss may also be a major cause of osteoporosis/bone loss in later life.

In accordance with an embodiment, the present invention provides a method for treating or prevention of the cessation of bone/growth or accrual in a pediatric or juvenile subject comprising increasing expression of Ezh2 expression in the primary spongiosa of the subject. It will be understood by those of ordinary skill in the art, that increasing the Ezh2 expression in the primary spongiosa in a pediatric or juvenile subject will result in Ezh2 downregulating cellular senescence by blocking demethylation of H3K27me3. In some embodiments, increasing the Ezh2 expression in the primary spongiosa can be through administration to the subject of an effective amount of growth hormone (GH).

In accordance with an embodiment, the present invention provides a method for treating or prevention of the cessation of bone/growth or accrual in a pediatric or juvenile subject comprising administering to the subject an effective amount of one or more H3K27 demethylase inhibitors to the subject.

In accordance with an embodiment, the present invention provides a method for treating or prevention of primary osteoporosis in a pediatric or juvenile subject comprising administering to the subject an effective amount of one or more H3K27 demethylase inhibitors to the subject.

As used herein, the term "pediatric or juvenile subject" means a mammalian subject which is prepubescent, or in early or late puberty." In some definitions, this can mean in humans, ages from before 12 years to 17, and up to as late as 24 years of age.

As used herein, the term "H3K27 demethylase inhibitors" means any biologically active agent which blocks demethylation of histone H3K27.

In accordance with some embodiments the composition GSK-J4 is a biologically active agent which blocks demethylation of histone H3K27.

As used herein, the term GSK-J4 means a compound having the following chemical formula:

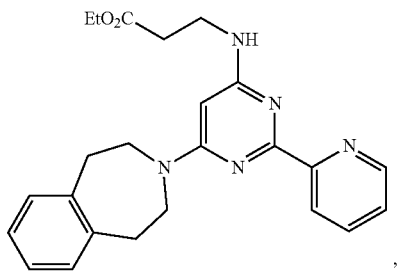 [SMILES: CCOC(=O)CCNc1cc(N2CCc3ccccc3CC2)nc(-c2ccccn2)n1]

corresponding to N-[2-(2-Pyridinyl)-6-(1,2,4,5-tetrahydro-3H-3-benzazepin-3-yl)-4-pyrimidinyl]-β-alanine ethyl ester, and accordingly, included within the compounds used in the methods of the present invention are the tautomeric forms of the disclosed compounds, isomeric forms including enantiomers, stereoisomers, and diastereoisomers, and the pharmaceutically-acceptable salts thereof.

The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

Embodiments of the present invention also include a process for preparing pharmaceutical products comprising the compounds disclosed herein. The term "pharmaceutical product" means a composition suitable for pharmaceutical use (pharmaceutical composition), as defined herein. Pharmaceutical compositions formulated for particular applications comprising the compounds of the present invention are also part of this invention, and are to be considered an embodiment thereof.

As used herein, the term "treat," as well as words stemming therefrom, includes preventative as well as disorder remitative treatment. The terms "reduce," "suppress," "prevent," and "inhibit," as well as words stemming therefrom, have their commonly understood meaning of lessening or decreasing. These words do not necessarily imply 100% or complete treatment, reduction, suppression, or inhibition.

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compounds disclosed herein. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

Generally, the ingredients are supplied either separately or mixed together in unit dosage form, for example, as a dry lyophilized powder or water-free concentrate in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration.

An article of manufacture containing materials useful for the treatment of the disorders described above is provided. The article of manufacture comprises a container and a label. Suitable containers include, for example, bottles, vials, syringes and test tubes. The containers may be formed from a variety of materials such as glass or plastic. The container holds a composition which is effective for preventing or treating, for example, a wound or a joint disease and may have a sterile access port (for example, the container may be a vial having a stopper pierceable by a hypodermic injection needle). The label on or associated with the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including buffers, diluents, filters, needles, syringes and package inserts with instructions for use.

For purposes of the invention, the amount or dose of the compounds, salts, solvates, or stereoisomers of any one the compounds disclosed herein, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compounds, salts, solvates, or stereoisomers of GSK-J4, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 100 ng/kg to about 10 g/kg body weight of the subject being treated/day, preferably about 20 mg/kg to about 1000 mg/kg body weight/day.

By "an effective amount" is meant the amount required to identify, diagnose, image, or ameliorate the symptoms of a disease relative in an untreated or treated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "disease" is meant any condition or disorder that damages or interferes with the normal function of a cell, tissue, or organ. Examples of such diseases include diseases which cause senescence of in the primary spongiosa region during the prepubertal, early or late pubertal phase of a subject that lead to primary or secondary osteoporosis in juvenile or young adult subjects.

Primary osteoporosis includes, for example osteogenesis imperfecta (OI) representing the prototypical primary osteoporosis of childhood and age related bone loss.

Secondary osteoporosis, the loss of bone mass is caused by certain lifestyle behaviors, diseases, or medications. The most common causes of secondary osteoporosis include exposure to glucocorticoid medications, hypogonadism (low levels of testosterone), alcohol abuse, smoking, gastrointestinal disease, hypercalciuria, and immobilization.

In pediatric or juvenile subjects, the vast majority of secondary osteoporosis stems from glucocorticoid medications. There is a growing list of secondary pediatric osteoporoses (i.e., osteoporosis caused by underlying diseases and/or their treatment), with most falling into two broad categories: glucocorticoid-treated diseases and the disorders which compromise normal weight-bearing and mobility such as, for example, cerebral palsy, Rett syndrome, Duchenne muscular dystrophy, spina bifida, and spinal muscular atrophy. Glucocorticoid-induced osteoporosis is the most common form of secondary osteoporosis. Long-term treatment of glucocorticoids has been widely used in the management of chronic inflammatory childhood illnesses such as rheumatoid disorders, Crohn's disease, nephrotic syndrome as well as rare genetic diseases such as Duchenne muscular dystrophy, for example.

In some embodiments, other autoimmune diseases can be present for which glucocorticoid treatment is indicated and which the methods of the present invention can be useful in the prevention or treatment of osteoporosis, including, but not limited to, alopecia areata, autoimmune hemolytic anemia, autoimmune hepatitis, dermatomyositis, diabetes type 1), some forms of juvenile idiopathic arthritis, glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, some forms of thyroiditis, some forms of uveitis, vitiligo, and granulomatosis with polyangiitis (Wegener's).

As used herein, the term "autoimmune disease" can mean diseases including inflammatory bowel disease (e.g., ulcerative colitis or Crohn's disease), rheumatoid arthritis, diabetes mellitus, celiac disease, autoimmune thyroid disease, autoimmune liver disease, Addison's Disease, Sjögren's Syndrome, transplant rejection, graft vs. host disease and host vs. graft disease. In certain embodiments, the autoimmune disease is a neurological autoimmune disease, such as multiple sclerosis. In certain embodiments the autoimmune disease is an inflammatory bowel disease, such as uncreative colitis or Crohn's disease. Examples of neurological autoimmune diseases include, for example, multiple sclerosis, Guillain-Barre syndrome, Lambert-Eaton myasthenic syndrome, myasthenia gravis, transverse myelitis, systemic lupus erythematosus (SLE or lupus), acute disseminated encephalomyelitis, vasculitis, Sjogren's syndrome, Graves' disease, autoimmune inner ear disease, narcolepsy, neuromyotonia, and schizophrenia.

In accordance with an embodiment, the present invention provides a method for treating or prevention of secondary osteoporosis in a pediatric or juvenile subject comprising administering to the subject an effective amount of one or more H3K27 demethylase inhibitors to the subject.

In some embodiments, the one or more H3K27 demethylase inhibitors can include, but is not limited to GSK-J4 and tautomers, isomers, enantiomers, stereoisomers, and diastereoisomers, and the pharmaceutically-acceptable salts thereof.

In accordance with an embodiment, the present invention provides a method for the treatment of prevention of pediatric osteoporosis in a subject comprising administering to the pediatric subject an effective amount of one or more H3K27 demethylase inhibitors.

In accordance with an embodiment, the present invention provides a method for the treatment of prevention of juvenile osteoporosis in a subject comprising administering to the juvenile subject an effective amount of one or more H3K27 demethylase inhibitors.

In accordance with an embodiment, the present invention provides a method for the treatment of prevention of pediatric or juvenile subject short stature in a pediatric or juvenile subject comprising administering to the pediatric or juvenile subject an effective amount of one or more H3K27 demethylase inhibitors.

In accordance with an embodiment, the present invention provides a method for treating or prevention of secondary osteoporosis in a pediatric or juvenile subject In accordance with an embodiment, the present invention provides a method for treating or prevention of secondary osteoporosis in a pediatric or juvenile subject having a chronic inflammatory childhood illness and undergoing glucocorticoid treatment comprising administering to the subject an effective amount of one or more H3K27 demethylase inhibitors to the subject.

In some embodiments, the one or more H3K27 demethylase inhibitors can include, but is not limited to GSK-J4 and tautomers, isomers, enantiomers, stereoisomers, and diastereoisomers, and the pharmaceutically-acceptable salts thereof.

In some embodiments, the one or more H3K27 demethylase inhibitors can include, but is not limited to GSK-J4 and tautomers, isomers, enantiomers, stereoisomers, and diastereoisomers, and the pharmaceutically-acceptable salts thereof.

In accordance with an embodiment, the present invention provides a method for treating or prevention of secondary osteoporosis in a pediatric or juvenile subject having one or more disorders which compromise normal weight-bearing and mobility comprising administering to the subject an effective amount of one or more H3K27 demethylase inhibitors to the subject.

In some embodiments, the one or more H3K27 demethylase inhibitors can include, but is not limited to GSK-J4 and tautomers, isomers, enantiomers, stereoisomers, and diastereoisomers, and the pharmaceutically-acceptable salts thereof.

In some embodiments of the above methods, the one or more H3K27 demethylase inhibitors can be in the form of a composition comprising an effective amount of the inhibitor and one or more pharmaceutically acceptable carriers.

In some embodiments of the above methods, the one or more H3K27 demethylase inhibitors can be a composition comprising an effective amount of GSK-J4 and one or more pharmaceutically acceptable carriers.

In some embodiments of the above methods, the one or more H3K27 demethylase inhibitors can be a composition comprising an effective amount of GSK-J4, one or more pharmaceutically acceptable carriers, and one or more additional biologically active agents which can remediate osteoporosis. Examples of such agents include, but are not limited to bisphonates, Vitamin D, Calcium, etc.

The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

In one embodiment, the compounds of the present invention provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all, or substantially all of the compound, is released immediately after administration.

In yet another embodiment, the compounds of the present invention can be delivered in a controlled release system. For example, the agent may be administered using intravenous infusion, an implantable osmotic pump, a transdermal patch, or other modes of administration. In an embodiment, a pump may be used. In one embodiment, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

The compounds included in the pharmaceutical compositions of the present invention may also include incorporation of the active ingredients into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In accordance with the present invention, the compounds of the present invention may be modified by, for example, the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection, than do the corresponding unmodified compounds. Such modifications may also increase the compounds' solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently, or in lower doses than with the unmodified compound.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

EXAMPLES

Micro-CT Analysis.

Mice femora were dissected, fixed overnight in 70% ethanol, and analyzed by high-resolution µCT (Skyscan 1172, Bruker MicroCT, Kontich, Belgium). We used NRecon image reconstruction software, version 1.6, (Bruker MicroCT), CTAn data-analysis software, version 1.9 (Bruker MicroCT), and CTVol 3-dimensional model visualization software, version 2.0, (Bruker MicroCT) to analyze parameters of the trabecular bone in the metaphysis and cortical bone in the mid-diaphysis. The scanner was set at 50 kVp, 201 mA, and a resolution of 12.64 mm/pixel. Cross-sectional images of the distal femur were used to perform 3-dimensional histomorphometric analysis of trabecular bone. The sample area selected for analyses was a 2-mm length of the metaphyseal secondary spongiosa, originating 1.0 mm below the epiphyseal growth plate and extending caudally. Cortical morphometry was analyzed within a 600-µm long section at mid-diaphysis of the femur and included measurements of average thickness and cross-sectional area.

Cell Sorting and Flow Cytometry Analysis

For flow cytometric analysis and sorting of CD45-GFP– and CD45-GFP+ mesenchymal progenitor cells (MPCs) from femoral metaphysis, we dissected the femora free of soft tissues from Nestin-GFP mice. The epiphysis was removed and only the 3-mm-long metaphysis regions were processed. The bone was then digested with a protease solution (2 mg/mL collagenase A and 2.5 mg/mL trypsin in phosphate buffered saline [PBS]) for 20 minutes to remove the periosteum and periosteal progenitors (step I). The bones were cut into small pieces and digested in the protease solution for another 1 hour (C, step II). Cells within the supernatant were collected for flow cytometry. After the process of red blood cell lysis with commercial ammonium-chloride-potassium lysis buffer (Quality Biological, Inc., Gaithersburg, Md.), CD45+ cells were removed by CD45 MicroBeads using MACS cell separation system (Miltenyi Biotec, San Diego, Calif.). Cells were then sorted according to side scatter and GFP expression after negative selection of CD45. FACS was performed using a 5-laser BD FACS and FACSDiva (Becton Dickinson Biosciences, San Jose, Calif.). Flow cytometric analyses were performed using a FACSCalibur flow cytometer and CellQuest software (Becton Dickinson Biosciences). The primary antibodies used were FITC-conjugated anti-GFP, PerCP-conjugated anti-CD45 (BioLegend, Inc., San Diego, Calif.). For flow cytometric analysis of LepR+ cells, antibody against leptin receptor (R&D Systems, Inc., Minneapolis, Minn.) was used, followed by incubation with Cy3-conjugated secondary antibody.

Immunocytochemistry and Immunofluorescence Studies.

For immunocytochemical staining, we incubated cultured cells with primary antibody to mouse p16Ink4A (Abcam ab10834,1:200), Ezh2 (Cell Signaling 5246S,1:200) at 4° C. overnight and subsequently used a horseradish peroxidase-streptavidin detection system (DAKO) or Alexa Fluor-coupled secondary antibody (Jackson ImmunoResearch Laboratories, Inc., West Grove, Pa.) to detect immunoreactivity. For bromodeoxyuridine (BrdU) assay, cultured cells were incubated with BrdU solution (10 µM) at 37° C. overnight, followed by immunocytochemical staining with primary antibody against BrdU (Abcam, ab6326, 1:100). Senescent cells were detected by senescence β-Galactosidase staining kit according to the manufacturer's instructions (Cell Signaling Technology, Danvers, Mass.).

At the time of euthanasia, the femora were resected and fixed in 4% paraformaldehyde solution for 4 hours, decalcified in 0.5M EDTA at 4° C. with constant shaking for 1 to 2 days and immersed into 20% sucrose and 2% polyvinylpyrrolidone solution for 24 hours. Finally, the tissues were embedded in optimal cutting temperature compound (Sakura Finetek USA, Inc., Torrance, Calif.) or 8% gelatin (porcine) in presence of 20% sucrose and 2% polyvinylpyrrolidone (PVP) solution (Kusumbe et al., 2015). Longitudinally oriented 10-µm-thick sections of bone, including the metaphysis and diaphysis, were processed for immunofluorescence staining.

For immunofluorescence staining, we incubated the sections with primary antibodies to mouse Ki67 (Novus Biologicals, NB500-170, 1:50), p16INK4a (Abcam ab10834,1:100), p21CIP1 (Abcam, ab109520,1:500), GFP (Rockland, 600-101-215,1:500 or Abcam, ab290,1:200), Nestin (Ayes Labs, NES, 1:100), Ezh2 (Cell Signaling 5246S,1:200), H3K27me3 (Cell Signaling, 9733S,1:800), osterix (Abcam, ab2252, 1:200), osteocalcin (Takara, M173, 1:200), endomucin (sc-65495, Santa Cruz, diluted 1:100), pecam1 (CD31) conjugated to Alexa Fluor 488 (R&D Systems, Inc., Minneapolis, Minn., FAB3628G, 1:100), leptin receptor (R&D Systems, Inc., Minneapolis, Minn., BAF497, 1:200), followed by incubation with FITC, or Cy3-conjugated secondary antibodies (Jackson ImmunoResearch). Nuclei were counterstained with DAPI (Sigma). The sections were mounted with the ProLong Antifade Kit (Molecular Probes, Eugene, Oreg.) and observed under a Fluo View 300 Confocal Microscope (Olympus America, Inc., Center Valley, Pa.).

Chromatin Immunoprecipitation (ChIP) and Antibodies.

ChIPs were performed according to conditions suggested by the manufacturer's EpiTect ChIP OneDay kit (Qiagen, Hilden, Germany) with ChIP-grade antibodies to H3K27me3 (Qiagen, Hilden, Germany). Briefly, formaldehyde was added to cells to cross-link proteins to DNA, and the cells were lysed in 1.5-mL lysis buffer (50 mM HEPES, pH 7.5, 140 mM NaCl; 1 mM EDTA; 1% Triton X-100; 0.1% sodium deoxycholate; 0.1% sodium dodecyl sulfate). Cell lysates were sonicated at the set of 2 seconds on/15 seconds off for 3 rounds using a Bioruptor ultrasonic cell disruptor (Diagenode, Denville, N.J.) to shear genomic DNA to an average fragment size of 150 to 250 bp. Of the sample, 1% was removed for use as an input control. ChIP was performed following protocol provided by EpiTect ChIP OneDay kit (Qiagen) using antibodies toward H3K27Me3 (Qiagen). Anti-RNA polymerase II and control IgG were used as positive and negative controls, respectively. After washing and de-crosslinking, the precipitated DNA was purified using a QIAquick PCR purification kit (Qiagen).

ChIP-qPCR

ChIP-qPCR was performed using SYBR Green PCR Master Mix and 7900 HT Fast Real-Time PCR System (Applied Biosystems Corp., Foster City, Calif.). Primers for p16, p21, P27, P15, bone morphogenetic protein-2, and bone morphogenetic protein-4 were used (see Table 1 for primer sequences). Absolute quantification was performed and enrichment expressed as a fraction of the whole-cell extract control.

(Biotek Instruments, Inc., Winooski, Vt.). RNA was reverse transcribed to complementary DNA using SuperScript III First Strand Synthesis System for RT-PCR (Invitrogen Corp., Carlsbad, Calif.) according to manufacturer's protocols. Customized mouse epigenetic chromatin modification enzymes RT$^2$ Profiler PCR array (Qiagen) was performed using SYBR Green PCR Master Mix and 7900 HT Fast Real-Time PCR System (Applied Biosystems Corp., Foster City, Calif.) and analyzed according to manufacturer's instructions. To validate the candidate genes screened from epigenetic chromatin modification enzymes PCR array, primers of Ezh2 and Ezh1 (see Table 2) were designed using primer bank database and Primer3, version 0.4.0, software (Whitehead Institute for Biomedical Research, Cambridge, Mass.). The amplification conditions were 95° C. for 10

TABLE 1

Primers used for ChIP-PCR

| Primers | Forward | Reverse |
|---|---|---|
| P15 | CTGCTTGGTCTAATGCTAACTGTG (SEQ ID NO: 1) | GGTCTTTATTTAGCTCAGGCCTGC (SEQ ID NO: 2) |
| P16-1 | CCCGGACTACAGAAGAGATG (SEQ ID NO: 3) | TCCGATCCTTTAGCGCTGTT (SEQ ID NO: 4) |
| P16-2 | ACACTCTGCTCCTGACCTGG (SEQ ID NO: 5) | AGGGGTGTTCAATTCATGCTAT (SEQ ID NO: 6) |
| P16-3 | GGAGCCACCCATTAAACTAACT (SEQ ID NO: 7) | CAAAAATAAGACACTGAAAACTCG (SEQ ID NO: 8) |
| P21 | CAGGACCAACCCACTCCTT (SEQ ID NO: 9) | CACAGTTGGTCAGGGACAGA (SEQ ID NO: 10) |
| P27 | GGCTCCCGTTAGACACTCTC (SEQ ID NO: 11) | CTGGCTCTGCTCCATTTGAC (SEQ ID NO: 12) |
| BMP2 | ACTGGTGGAGTGGAGTGGAC (SEQ ID NO: 13) | CTGGGGTTTGGAATGCCTAA (SEQ ID NO: 14) |
| BMP4 | CAGTTTATGGAAGGCCACCT (SEQ ID NO: 15) | GTAACTGCTGCCCAAACTGA (SEQ ID NO: 16) |

RNA Extraction and Mouse Epigenetic Chromatin Modification Enzymes PCR Array.

FACS-sorted CD45-GFP+ and CD45-GFP− mesenchymal progenitor cells in metaphysis of femora from 4-week-old Nestin-GFP mice were harvested, and total RNA was isolated using RNeasy Mini kit (Qiagen). RNA samples were assessed for quality and integrity using Synergy HT minutes, 95° C. for 15 seconds, and 60° C. for 1 minute. No-template and no-RT controls were included for each assay to ensure quality and complementary DNA specificity of the primers. Target-gene expression was normalized to glyceraldehyde 3-phosphate dehydrogenase (GAPDH) messenger RNA and relative gene expression assessed using the $2^{-\Delta\Delta CT}$ method.

TABLE 2

Primers used for quantitative real-time PCR

| Primers | Forward | Reverse |
|---|---|---|
| P16 | GAAAGAGTTCGGGGCGTTG (SEQ ID NO: 17) | GAGAGCCATCTGGAGCAGCAT (SEQ ID NO: 18) |
| P21 | AGAAGGTACTTACGGTGTGGT (SEQ ID NO: 19) | GAGAGATTTCCCGAATTGCAGT (SEQ ID NO: 20) |
| P53 | ATCGCCTTCGACATCATCGC (SEQ ID NO: 21) | CCCCATGCGTACTCCATGAG (SEQ ID NO: 22) |
| Ki67 | ACCGTGGAGTAGTTTATCTGGG (SEQ ID NO: 23) | TGTTTCCAGTCCGCTTACTTCT (SEQ ID NO: 24) |

TABLE 2-continued

Primers used for quantitative real-time PCR

| Primers | Forward | Reverse |
| --- | --- | --- |
| Ezh1 | CCAGACTGCCAGAATCGCTTT (SEQ ID NO: 25) | CAGGTGCTTTTTGAGGCCA (SEQ ID NO: 26) |
| Ezh2 | AGTGACTTGGATTTTCCAGCAC (SEQ ID NO: 27) | AATTCTGTTGTAAGGGCGACC (SEQ ID NO: 28) |
| UTX | CGGGCGGACAAAAGAAGAAC (SEQ ID NO: 29) | CATAGACTTGCATCAGATCCTCCA (SEQ ID NO: 30) |

Statistics.

Data are presented as means±standard errors of the mean. Unpaired, 2-tailed Student's t-tests were used for comparisons between 2 groups. For multiple comparisons, 1-way analysis of variance (ANOVA) with Bonferroni post hoc test was applied. All data were normally distributed and had similar variation between groups. Statistical analysis was performed using SAS version 9.3 software (SAS Institute, Inc., Cary, N.C.). P<0.05 was deemed significant.

Example 1

Cells in Primary Spongiosa of Long Bone Undergo Programmed Senescence During Late Puberty.

Mouse pubertal growth can be divided into an early pubertal phase (3 to 5 weeks of age) and a late pubertal phase (5 to 8 weeks of age) (Callewaert et al., 2010). We first assessed the rate of long bone growth in mice at different postnatal stages by measuring the femur lengths and calculating the elongation rates. Bone growth was fast during prepuberty and early puberty periods (2-5 weeks of age), became slow during late puberty (6-8 weeks of age), and almost stopped during young adulthood (8-12 weeks of age) in both female and male (data not shown). We then conducted exploratory SA-βGal staining in femoral bones of mice at a chosen age in each bone growth phase. A significant increase in the number of SA-βGal+ cells was observed only in primary spongiosa (i.e., trabecular bone adjacent to the growth plate) of the femur bones in 6- and 8-week old male mice relative to 4-week old mice, whereas the SA-βGal+ senescent cells diminished at the same region of femoral bone in 12-week old male mice (FIG. 1A-1C). SA-βGal+ cells were barely detectable in secondary spongiosa and the diaphyseal bone marrow in mice at any ages detected (FIG. 1D-1E), indicating that senescence in pubertal bone is a time- and location-restricted event. Similar localization and time-course of cellular senescence was also observed in the femoral bone of female mice (data not shown). Consistently, at 4 weeks (early pubertal phase), cells at the primary spongiosa were highly positive for the proliferation marker Ki67 (FIGS. 1F and 1G). However, at 6 and 8 weeks (late pubertal phase), Ki67 staining was dramatically reduced in the same region. At 12 weeks, whereas SA-βGal+ senescent cells were almost undetectable, Ki67+ cells were restored in femoral primary spongiosa, indicating a strong association between SA-βGal activity and the absence of proliferation. Thus, cells in primary spongiosa of long bones undergo senescence-like growth arrest during late puberty when the bone growth rate starts to decline Example 2

Senescent Cells in Primary Spongiosa is Characterized by Loss of Nestin Expression.

Nestin has been shown to be required for self-renewal, proliferation and cell cycle progression of the cells (Hu et al., 2016; Park et al., 2010; Sahlgren et al., 2003; Sahlgren et al., 2006). In adult bone, cells expressing GFP in response to a nestin promoter/enhancer (Nestin-GFP) and those expressing NescreER are heterogeneous precursor cells mainly in endothelial and mesenchymal lineage (Itkin et al., 2016; Méndez-Ferrer et al., 2010; Ono et al., 2014a). We detected a progressive reduction of Nestin-GFP signaling in Nestin-GFP mice (FIGS. 2A and 2B) and nestin+ cells in C57BL/6 mice (data not shown) specifically in femoral primary spongiosa in 6- and 8-week old mice, coincident with the occurrence of senescent cells at the same region of long bone. We isolated mesenchymal progenitor cells (MPCs) from both bone marrow and endosteal bone surface in femoral metaphysis (including primary and secondary spongiosa) using an established enzymatic digestion approach (Siclari et al., 2013) because isolating cells from primary spongiosa has technical difficulty.

Generally, Femur of mice were collected. The end of distal femur was removed at growth plate site, and the remaining bone were cut at 3 mm from the growth plate, and this piece of bone at the end was considered as metaphyseal region. To isolate cells from the metaphyses, the bones were then digested with a protease solution (2 mg/ml collagenase A and 2.5 mg/ml trypsin in PBS) for 20 min to remove the periosteum and periosteal progenitors (Step I). The bones were cut into small pieces and digested in the protease solution for another 1 h (Step II). Cells within the supernatant were collected for flow cytometry and the sorted cells were plated for expending. The adherent cells were considered as CD45-GFP+ and CD45-GFP− MPCs, which were used for further culture and analysis.

Figures 2A, 2B, 2C, 2D, 2E, 2F, 2G, 2H:
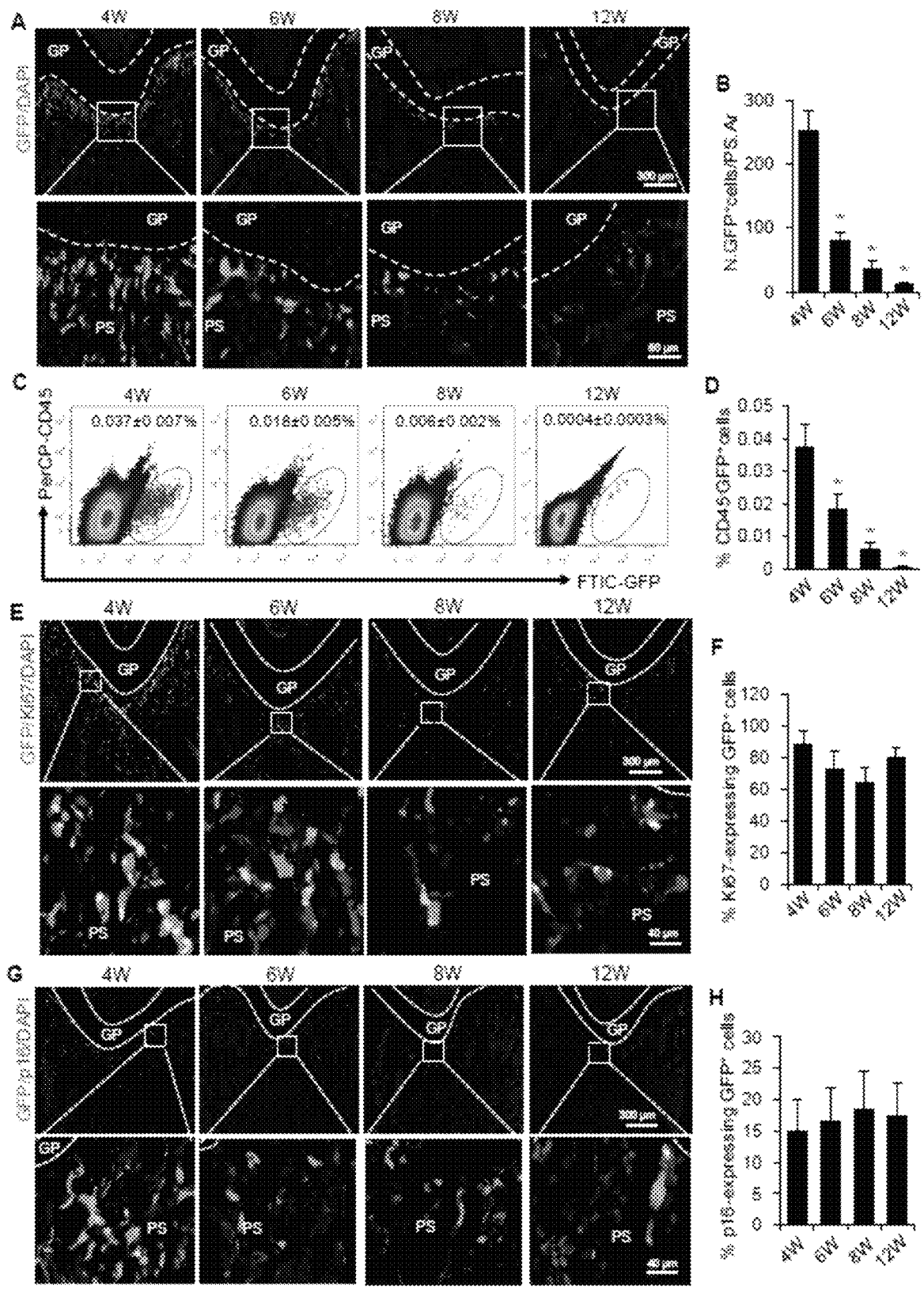
FIGS. 2A-2H. Senescent Cells in Primary Spongiosa of Long Bones are Concomitant with Loss of Nestin Expression. (2A-2B) Representative images of GFP immunofluorescence staining and quantitative analysis of GFP+ cells in femoral primary spongiosa from 4, 6, 8, 12-week-old male Nestin-GFP mice. Images in upper panels in (2A) are lower power with boxes outlining the area of higher power in lower panels. Numbers of GFP+ cells per mm$^2$ tissue area in primary spongiosa (N. GFP+ cells/PS.Ar) (2B). (2C-2D) Representative images of the flow cytometry analysis and the percentage of the CD45-GFP+ cells in femoral metaphysis from 4, 6, 8, 12-week-old male Nestin-GFP mice. (2E-2H) Double-immunofluorescence images of femoral metaphysis sections from 4, 6, 8, 12-week-old male Nestin-GFP mice using antibodies against GFP (green) and either Ki67 (red) (2E) or p16 (red) (2G) respectively. DAPI stains nuclei blue. Images in upper panels in (2E) and (2G) are lower power with boxes outlining the area of higher power in lower panels. Quantification of the percentage of GFP+ cells that express Ki67 (2F) or p16 (2H) are shown, respectively. Five mice per group. Data are represented as mean±s.e.m. GP, growth plate. PS, primary spongiosa. *p<0.05 as determined by ANOVA.
Figures 3A, 3B, 3C, 3D, 3E, 3F, 3G, 3H, 3I, 3J, 3K:
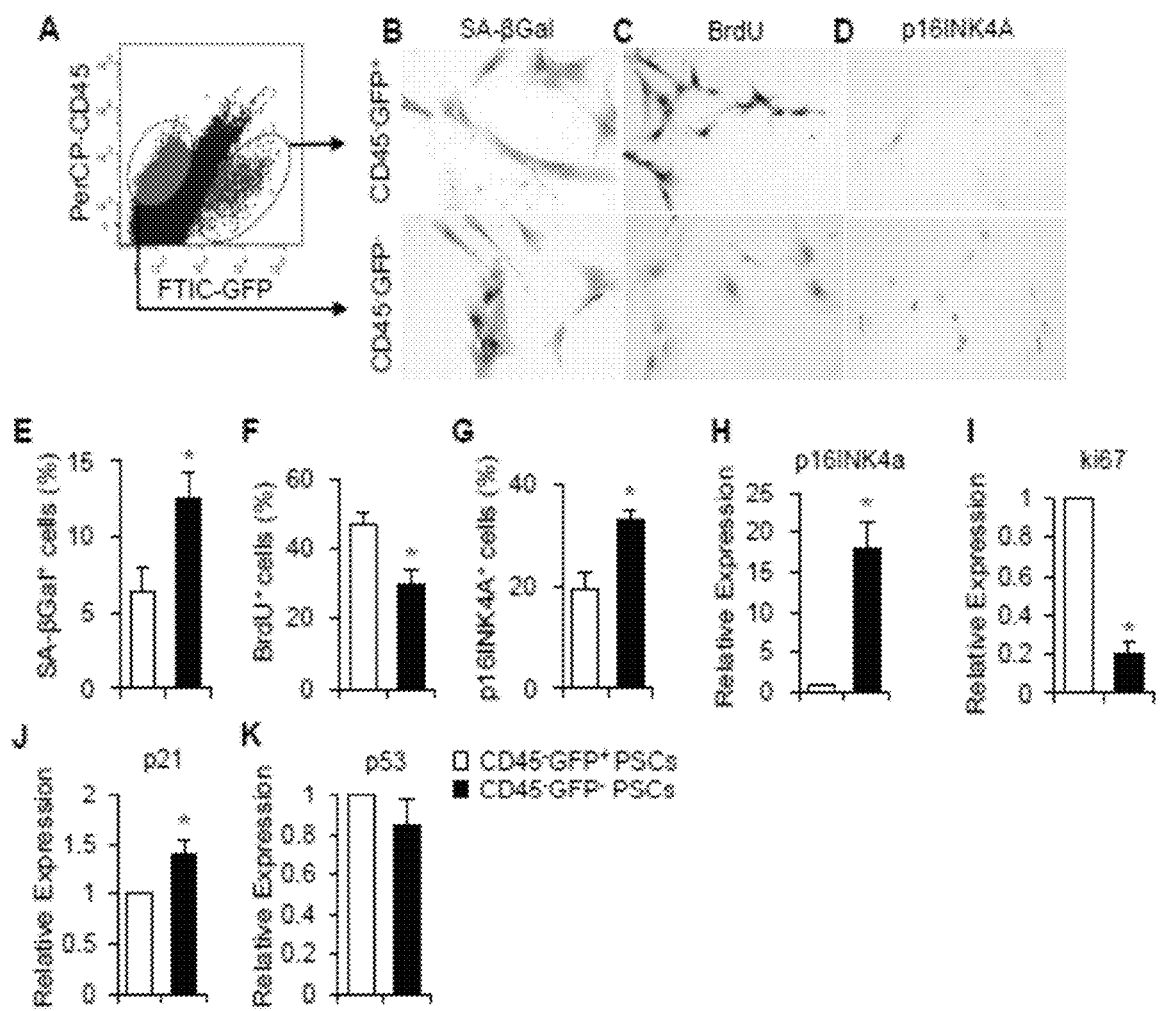
FIGS. 3A-3K. Cellular Senescence Occurs in Nestin-GFP−Cells But Not in Nestin-GFP+ Cells in Femoral Metaphyses. (3A) Diagrams showing the isolation of Nestin-GFP+ and Nestin-GFP− mesenchymal progenitor cells (MPCs) by fluorescence-activated cell sorting. Detailed information on the isolation of MPCs from femoral Metaphyses from Nestin-GFP mice were described in the methods section. (3B-3D) The sorted cells were cultured, and the SA-βGal staining (3B), BrdU incorporation (3C), and p16INK4A immunostaining (3D) were performed, and representative images were shown. (3E-3G) Quantification of the percentage of the cells that express SA-βGal (3E), BrdU (3F) and p16INK4A (3G). (3H-3K) Quantitative RT-PCR analysis of p16INK4a (3H), ki67 (3I), p21 (3J), p53 (3K) expression in the sorted CD45-GFP+ and CD45-GFP− MPCs. Eight mice per group. Data are represented as mean±s.e.m.*
Figures 5A, 5B, 5C, 5D, 5E, 5F, 5G, 5H, 5I, 5J, 5K, 5L:
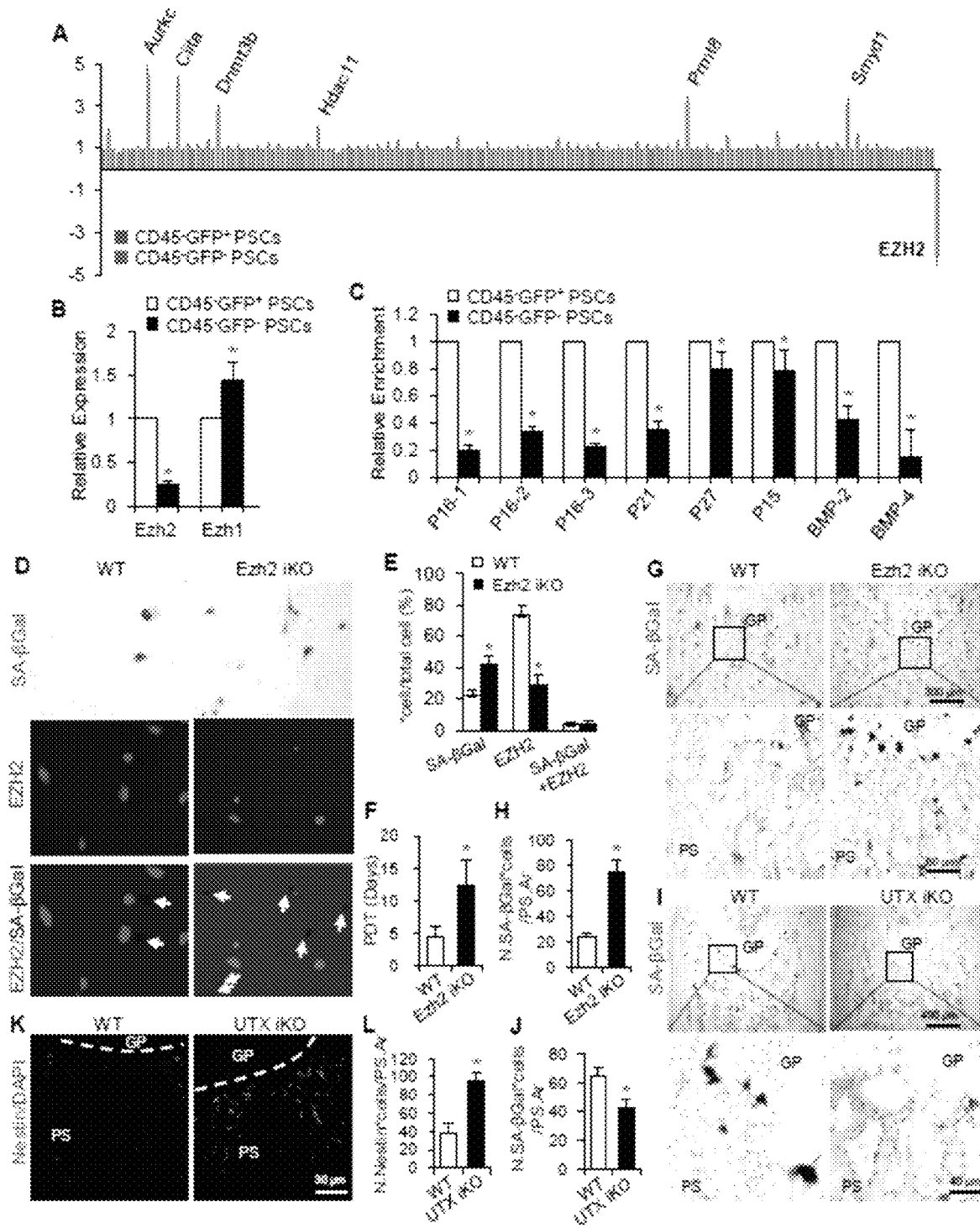
FIGS. 5A-5L. Ezh2-H3K27me3 Regulates Progression of Cellular Senescence in Primary Spongiosa of Long Bone. (5A) CD45-GFP+ and CD45-GFP− mesenchymal progenitor cells (MPCs) were separately isolated from femoral metaphyses from 4-week-old Nestin-GFP mice, and the total RNA was subjected for PCR array analysis of the chromatin modification enzymes. (5B) Validation of the messenger RNA changes of the indicated genes by qRT-PCR analysis. (5C) CD45-GFP+ and CD45-GFP− mesenchymal progenitor cells (MPCs) were isolated separately. Chromatin immunoprecipitation (ChIP) with H3K27me3 antibody was then performed. ChIP and input DNA were measured using real-time PCR with specific primers targeting the promoter regions of the indicated genes (n=3). Data are represented as mean±s.e.m. *p<0.01 as determined by Student's t tests. (5D-5F) Four-week-old male Nestin-CreERT2::Ezh2 flox/flox (Ezh2 iKO) mice and Nestin-CreERT2 mice (WT) were injected with 1 dose of tamoxifen (100 mg/kg·B·W.). Mesenchymal progenitor cells (MPCs) were then isolated. Costaining of the SA-βGal and Ezh2 expression indicates that SA-βGal and Ezh2 are mutually expressed in cells (5D). White arrows represent SA-βGal+ cells in merged images. Quantification of the percentage of the cells that express SA-βGal, Ezh2, or both (5E). Population Doubling Time (PDT) of the cells was measured (5F). (5G, 5H) Three-week-old male Nestin-CreERT2::Ezh2 flox/flox (Ezh2 iKO) mice and Nestin-CreERT2 mice (WT) were injected with 3 doses of tamoxifen (100 mg/kg·B·W., every other day). Representative SA-βGal staining and quantitative analysis of SA-βGal+ cells in femoral primary spongiosa from the mice. Numbers of the SA-βGal+ cells per mm$^2$ tissue area in primary spongiosa (N. SA-βgal+ cells/PS.Ar). (5I-5L) Six-week-old female Nestin-CreERT2::UTXflox/flox (UTX iKO) mice and Nestin-CreERT2 mice (WT) were injected with tamoxifen for 2 weeks (100 mg/kg·B·W., 3 doses during the first week, and 1 dose during the second week). Representative SA-βGal staining (5I) and quantitative analysis of SA-βGal+ cells (5J) in femoral primary spongiosa from the mice. Number of SA-βGal+ cells per mm$^2$ tissue area in primary spongiosa (N. SA-βgal+ cells/PS.Ar). Representative immunofluorescence staining using antibodies against nestin (5K) and quantitative analysis of nestin+ cells (5L) in femoral primary spongiosa from the mice. Number of nestin+ cells per mm$^2$ tissue area in primary spongiosa (N. nestin+ cells/PS.Ar). Five mice per group. Data are represented as mean±s.e.m. GP, growth plate. PS, primary spongiosa. *p<0.01 as determined by Student's t-tests.

Consistent with the immunofluorescence staining results, flow cytometry analysis of the isolated cells showed that the percentage of CD45-GFP+ cells was gradually reduced in mice of 6 to 12 weeks of age (FIGS. 2C and 2D). We reasoned that cells expressing nestin may represent highly proliferative cells, and the cellular senescence in this region during late puberty may be the result of a gradual loss of nestin expression. Indeed, double immunofluorescence staining showed that most of Nestin-GFP+ cells (about 84%) expressed proliferation marker Ki67 (FIGS. 2E and 2F), and only a small proportion of Nestin-GFP+ cells expressed senescence marker p16INK4a in primary spongiosa (FIGS. 2G and 2H). To further document the correlation of loss of nestin expression with cellular senescence, CD45-GFP+ and CD45-GFP− MPCs were isolated, respectively, from the femoral metaphysis from 6 weeks old mice (FIG. 3A). CD45-GFP− MPCs, relative to CD45-GFP+ MPCs, had increased SA-βGal+ cells (FIGS. 3B and 3E), less BrdU-labeling (FIGS. 3C and 3F), and more cells positive for cellular senescence marker p16INK4a (FIGS. 3D and 3G). We examined the expression of known markers and mediators of senescence in these 2 cell populations by quantitative RT-PCR (qRT-PCR). A nearly 18-fold increase in p16INK4a expression (FIG. 3H) and more than 5-fold decrease in Ki67 expression (FIG. 3I) were detected in CD45-GFP− MPCs compared with those in CD45-GFP+ MPCs. Expression of another senescence inducer p21CIP1 (CDKN1A) was also significantly increased in the CD45-GFP− MPCs vs. the CD45-GFP+ MPCs (FIG. 3J). However, no difference of the expression of p53, a tumor suppressor that controls the senescence response to tissue damage or cancer-causing stress, was seen in these 2 cell populations (FIG. 3K). Therefore, nestin expression maintains active proliferative property of the cells, whereas loss of nestin expression in MPCs represents a distinctive feature for senescence-like cell cycle arrest in metaphysis region of long bone in late puberty. We found that most of GFP+ cells (about 82%) expressed osteoprogenitor marker osterix (Osx), and 11% of GFP+ cells expressed endothelial marker endomucin (Emcn) (data not shown). Interestingly, leptin receptor (LepR) + cells, multipotent MPCs that give rise to most bone and adipocytes in adult bone marrow (Yue et al., 2016; Zho u et al., 2014), exhibited an opposite expression pattern to nestin+ cells in femoral metaphysis. The number of LepR+ cells gradually increased in primary spongiosa in femora from 4 to 12 weeks of age, as detected by immunofluorescence staining (data not shown) and flow cytometry analysis (FIG. 5E).

Example 3

Cellular Senescence in Primary Spongiosa of Long Bone is Associated with Bone Growth/Accrual.

Figures 4A, 4B, 4C, 4D, 4E, 4F, 4G, 4H, 4I, 4J, 4K, 4L:
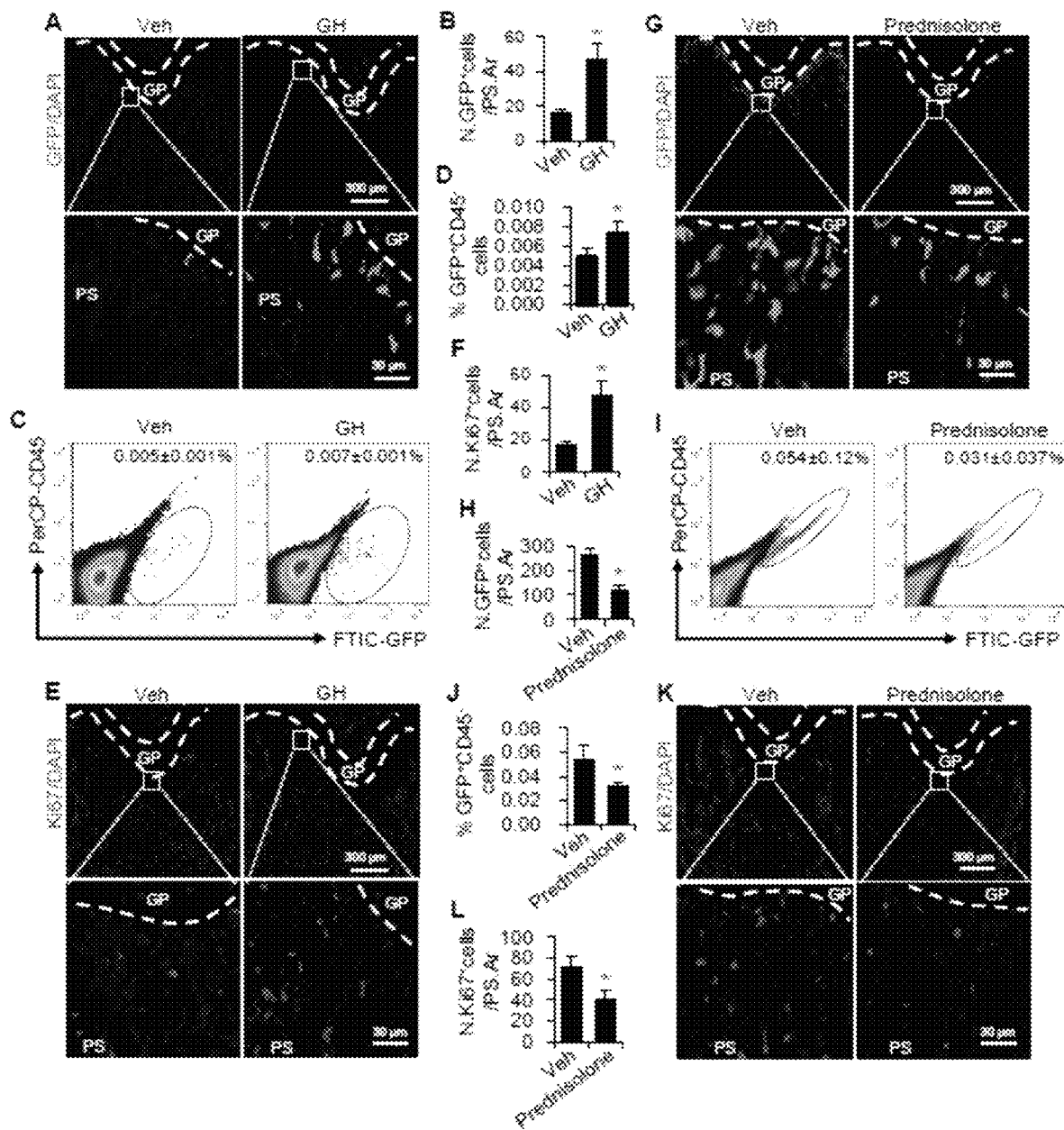
FIGS. 4A-4L. Cellular Senescence in Primary Spongiosa of Long Bone is Decelerated in Growth Hormone (GH)-Treated Mice and Accelerated in Prednisolone-Treated Mice. (4A-4F) Four week-old Nestin-GFP mice were treated with recombinant mouse-GH (5 mg/kg·B·W.) or Vehicle by daily intraperitoneal injection for 4 weeks. Immunofluorescence staining of femur sections were performed using antibodies against GFP (green) (4A) or Ki67 (red) (4E). Images in upper panels in (4A) and (4E) are lower power with boxes outlining the area of higher power in lower panels. Quantification of the number of GFP+ (4B) or Ki67+ (4F) cells in femoral primary spongiosa. Representative images of flow cytometry analysis and the quantification of the percentage of the CD45-GFP+ cells isolated from femoral metaphysis (4C-4D). (4G-4L) Two-week-old Nestin-GFP mice were treated with prednisolone (10 mg/m$^2$/day) or Vehicle by daily intraperitoneal injection for 2 weeks. Immunofluorescence staining of femur sections were performed using antibodies against GFP (green) (4G) or Ki67 (red) (4K). Images in upper panels in (4G) and (4K) are lower power with boxes outlining the area of higher power in lower panels. Quantification of the number of GFP+ (4H) or Ki67+ (4L) cells in femoral primary spongiosa. Representative images of flow cytometry analysis and the quantification of the percentage of the CD45-GFP+ cells isolated from femoral metaphysis (4I-4J). Five mice per group. Data are represented as mean±s.e.m. GP, growth plate. PS, primary spongiosa. *p<0.01 as determined by Student's t-tests. p<0.01 as determined by Student's t-tests.

We tested whether the progression of the cellular senescence in primary spongiosa of long bone, as indicated by loss of nestin expression, is associated with bone growth/accrual. Growth hormone (GH) is critical to longitudinal skeletal growth during the postnatal and pubertal periods (Kristensen et al., 2010). An increase in bone mass during puberty is controlled largely by GH/insulin-like growth factor 1 (IGF-1) axis (Wang et al., 2015b; Wu et al., 2015). We assessed changes in nestin expression in the femoral primary spongiosa in pubertal mice after administration of recombinant GH. Daily injection of GH into early pubertal mice (4 weeks old) for 4 weeks significantly increased Nestin-GFP+ cells in primary spongiosa in late pubertal mice (8 weeks old) compared with vehicle-treated mice as detected by immunofluorescence staining (FIGS. 4A and 4B). Similar results were obtained by flow cytometry analysis of the percentage of CD45-GFP+ cells in the metaphysis MPCs (FIGS. 4C and 4D). Consistently, the percentage of Ki67+ proliferative cells in the same region was higher in GH-treated mice relative to vehicle-treated mice (FIGS. 4E and 4F).

One of the major causes of secondary osteoporosis in children is the use of glucocorticoids for treatment of underlying chronic medical problems, such as autoimmune or inflammatory disorders. Long-term use of glucocorticoids impairs skeletal growth and accelerates bone loss in children (Rizzoli and Biver, 2015). We thus assessed whether glucocorticoid-treated early pubertal mice display premature cellular senescence in primary spongiosa by injecting mice daily with prednisolone from age 2 weeks to 4 weeks. The number of Nestin-GFP+ cells in femoral primary spongiosa was significantly reduced in prednisolone-treated mice relative to vehicle-treated mice as assessed by immunofluorescence staining and flow cytometry analysis (FIG. 4G-4J). Prednisolone treatment also reduced Ki67+ proliferative cells (FIGS. 4K and 4L) in the same region of the femur. The results suggest that cellular senescence in primary spongiosa of long bone changes with the speed of bone growth during puberty.

Example 4

Progression of Cellular Senescence in Primary Spongiosa of Long Bone is Controlled by Ezh2-H3K27me3.

To examine whether spatiotemporal-restricted cellular senescence is associated with epigenetic changes, we isolated CD45-GFP+ and CD45-GFP− MPCs from the femoral metaphysis of 6 weeks old mice. Profiling the expression of 86 key genes encoding enzymes that modify genomic DNA and histones showed 12 differentially expressed genes in these 2 cell populations (1 downregulated and 11 upregulated; FIG. 5A). Among these genes, Ezh2, a histone methyltransferase within the PcG protein complex and that specifically catalyzes H3K27me3, was the only enzyme showing significant down-regulation in CD45-GFP− MPCs relative to CD45-GFP+ MPCs. Consistently, further qRTPCR analysis showed more than 4-fold reduction in the expression of Ezh2 in CD45-GFP− MPCs compared with that in CD45-GFP+ MPCs (FIG. 5B). On the contrary, the expression of Ezh1, another histone methyltransferase within PcG protein complex that also targets H3K27, increased in CD45-GFP− MPCs versus CD45-GFP+ MPCs, indicating that elevated Ezh1 may play a compensatory role in preventing the complete loss of H3K27me3 in the cells.

To examine whether Ezh2 regulates cellular senescence by demethylating H3K27me3, we performed chromatin immunoprecipitation (ChIP) assays to assess changes in histone methylation status at the promoter regions of the key genes involved in cell senescence and cell cycle arrest. We found that the promoter regions of the cell senescence inducer genes p16INK4a and p21CIP1 were enriched in H3K27me3 in the Nestin-GFP+ MPCs isolated from the femoral metaphysis whereas this histone modification on p16INK4a (approximately 4.2-fold) and p21CIP1 (approximately 2.8-fold) was dramatically decreased in Nestin-GFP− MPCs (FIG. 5C). H3K27me3 levels were also reduced at the promoter of cyclin-dependent kinases (cdks) inhibitors p27KIP1 and p15INK4b, but the degrees of the reductions were not as dramatic as those of p16INK4a and p21CIP1. BMP2-Smad signaling has been reported to mediate cellular senescence (Anai, 2011). We found that the H3K27me3 mark at the promoter regions of BMP2 (approximately 2.4-fold) and BMP4 (approximately 6.8-fold) was also remarkably reduced in Nestin-GFPMPCs relative to Nestin-GFP+ MPCs (FIG. 5C). Therefore, Ezh2-mediated H3K27me3 maintains the repression of many cell senescence genes and cell cycle inhibitor genes, and loss of Ezh2-H3K27me3 leads to activation of these genes for cellular senescence.

To further examine whether Ezh2-H3K27me3 is required for maintaining the Nestin+ cells in primary spongiosa of long bone during early puberty, we generated an inducible Nestin-CreERT2::Ezh2 flox/flox (Ezh2 iKO) mouse model by crossing Ezh2flo x/flox mice with Nestin-CreERT2 mice.

In Ezh2 iKO mice, Ezh2 was deleted specifically in nestin+ cells in a Tamoxifen-dependent manner. We first assessed whether deletion of Ezh2 in nestin+ cells during early puberty causes senescence of these cells in primary spongiosa of long bones by administering a single dose of tamoxifen in 3-week-old Nestin-CreERT2 (WT) and Ezh2 iKO mice and isolated the MPCs from metaphysis region of femoral bone 1 week later. Although most cells isolated from WT mice were Ezh2-positive (>75%), fewer than 30% of the cells from the Ezh2 iKO mice expressed Ezh2 (FIGS. 5D and 5E). The results suggest that Ezh2 was deleted in more than half of the MPCs at metaphyseal bone with one dose of Tamoxifen. The percentage of SA-βGal+ cells in the Ezh2 iKO mice was more than double that in WT mice (FIGS. 5D and 5E). The expressions of Ezh2 and SA-βGal were mutually exclusive in the cells, indicating a critical role of Ezh2 in preventing cellular senescence. The population doubling time of the cells isolated from Ezh2 iKO mice was longer compared with those from WT mice, indicating slower growth rate (FIG. 5F). To further document the role of Ezh2-modulated H3K27me3 in protecting the cells from senescence, we injected 3 doses of tamoxifen (every other day) into 3-week-old WT and Ezh2 iKO mice. Dramatically elevated SA-βGal+ senescent cells were detected in femoral primary spongiosa of the Ezh2 iKO mice compared with those in the WT mice (FIGS. 5G and 5H).

The X chromosome-encoded histone demethylase UTX (also known as KDM6A) mediates removal of repressive H3K27me3 to establish transcriptionally permissive chromatin. The inventors examined whether the increased H3K27me3 level in nestin+ cells is sufficient to decelerate the senescence of nestin+ cells in primary spongiosa of long bone during late puberty, we employed an inducible KO mouse that specifically ablates UTX in nestin+ cells, i.e., Nestin-CreERT2;UTXflox/flox mice (UTX iKO). UTY is the Y-chromosome homolog of UTX and has overlapping redundancy with UTX in embryonic development. To eliminate the potential for confounding effects of UTY function in these experiments, we used female mice to analyze cellular senescence. Six-week-old female UTX iKO mice and Nestin-CreERT2 (WT) mice were injected with tamoxifen for 2 weeks (3 doses in the first week, and 1 dose in the second week). Dramatically reduced SA-βGal+ senescent cells were detected in femoral primary spongiosa of the UTX iKO mice compared with those in the WT mice (FIGS. 5I and 5J). Furthermore, increased number of nestin+ cells in primary spongiosa were detected in the UTX iKO mice (FIGS. 5K and 5L). The results suggest that Ezh2-mediated H3K27me3 functions to maintain highly proliferative nestin+ cells in primary spongiosa of long bone in fast-growing bone, whereas loss of Ezh2-H3K27me3 in this region during late puberty results in loss of nestin expression and cellular senescence.

Example 5

Deletion of Ezh2 in Nestin+ Cells During Early Puberty Results in Diminished Vascularization and Osteogenesis in Primary Spongiosa, as well as Bone Loss in Later Life.

Figures 6A, 6R:
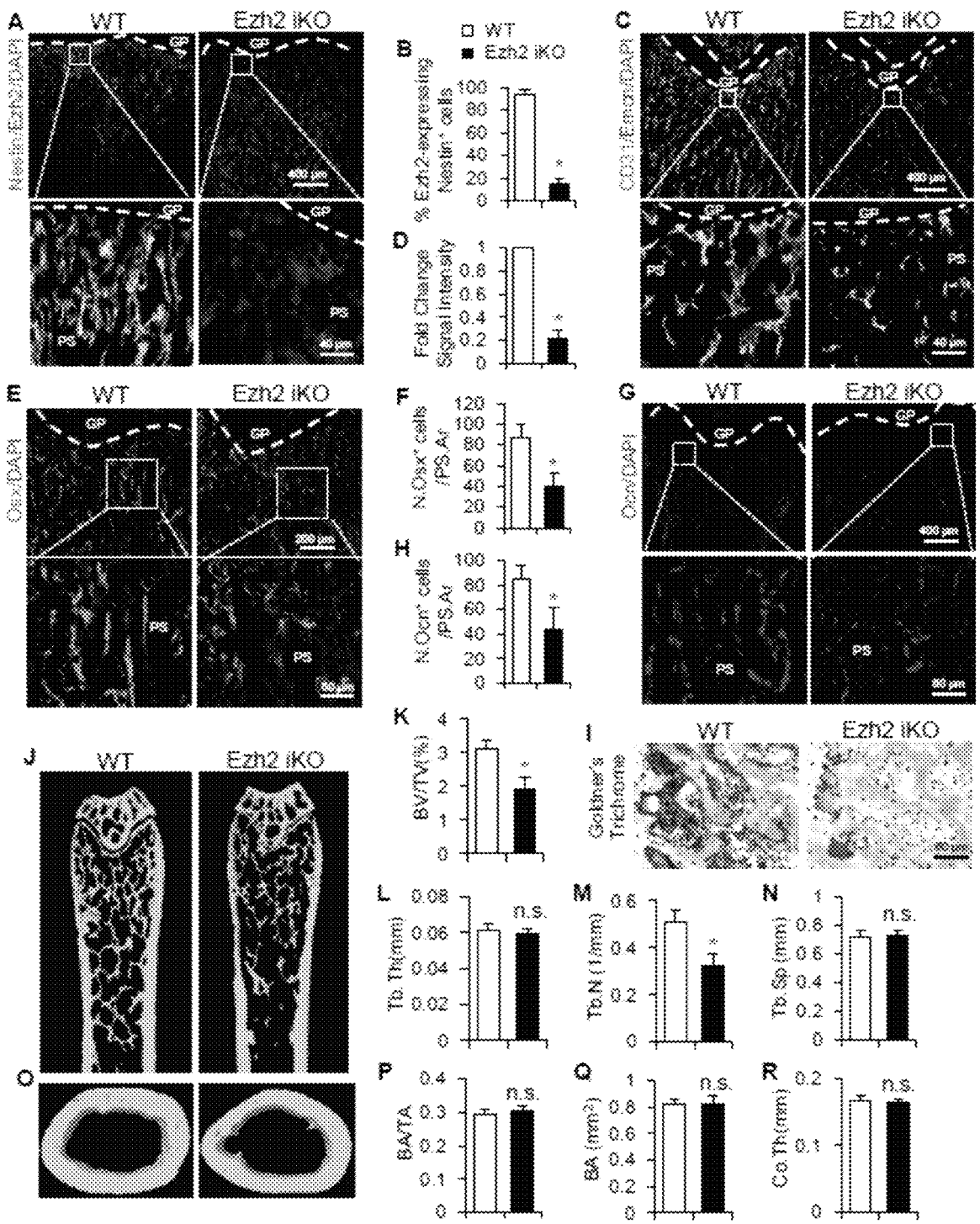
FIGS. 6A-6R. Deletion of EZH2 in Nestin+ Cells During Early Puberty Results in Diminished Vascularization and Osteogenesis in Metaphyseal Bone, as well as Bone Loss in Later Life. (6A-6I) Three-week-old male Nestin-CreERT2:: Ezh2 flox/flox (Ezh2 iKO) mice and Nestin-CreERT2 mice (WT) were injected with 3 doses of tamoxifen (100 mg/kg·B·W., every other day). The mice were humanely killed at 4 weeks of age. Double-immunofluorescence staining of femoral metaphysis sections was performed using antibodies against nestin (green) and Ezh2 (red) (6A). Quantification of the percentage of nestin+ cells that express Ezh2 in primary spongiosa (6B). Double-immunofluorescence staining of femur sections was performed using antibodies against CD31 (green) and endomucin (Emcn) (red) (6C). Quantitative analysis of relative fluorescence intensities in primary spongiosa (6D). Immunofluorescence staining of femur sections using antibodies against osterix (Osx) (6E) and osteocalcin (Ocn) (6G). DAPI stains nuclei blue. Quantitative analysis of Osx+ and Ocn+ cells in primary spongiosa is shown in (6F) and (6H), respectively. Five mice per group. Data are represented as mean±s.e.m. *p<0.05 as determined by Student's t-tests. Representative images of trichrome staining of the metaphyseal trabecular bone (6I). (6J-6R) Three-week-old male Nestin-CreERT2::Ezh2 flox/flox (Ezh2 iKO) mice and Nestin-CreERT2 mice (WT) were injected with 3 doses of tamoxifen (100 mg/kg·B·W., every other day). The mice were humanely killed at 16 weeks of age. Representative μCT images of distal femur were shown in (6J). Quantitative analyses of Trabecular bone volume fraction (BV/TV) (6K), trabecular thickness (Tb.Th) (6L), trabecular number (Tb.N) (6M) and trabecular separation (Tb.Sp) (6N). Representative μCT images of cross-sections of femoral mid-diaphysis (6O). The ratio of cortical bone area per total area (BA/TA) (6P), cortical bone area (BA) (6Q) and cortical bone thickness (Co.Th) (6R). Ten mice per group; GP, growth plate. PS, primary spongiosa. Data are represented as mean±s.e.m. *p<0.05 as determined by Student's t-tests.

It has been reported that Nestin-CreER labels vascular endothelial lineage cells and osteoprogenitor cells (Itkin et al., 2016; Méndez-Ferrer et al., 2010; Ono et al., 2014a). We assessed whether Ezh2 deletion in nestin+ cells during early puberty causes alterations of blood vessels and osteogenesis in the primary spongiosa of femora during late puberty. After 3 doses of tamoxifen administration (every other day) into 3-week-old WT and Ezh2 iKO mice, we assessed the bone phenotype in mice at 4 weeks of age. Although nestin+ cells were abundant in primary spongiosa of femoral bone in WT mice, these cells dramatically decreased in Ezh2 iKO mice (FIGS. 6A and 6B). CD31+ Emcn+ blood vessels in primary spongiosa, which are considered to be osteogenesis-coupled vessels (Kusumbe et al., 2014; Ramasamy et al., 2014; Xie et al., 2014), were also dramatically reduced in the Ezh2 iKO mice relative to WT mice (FIGS. 6C and 6D). A similar reduction in the Osx+ osteoprogenitor cells (FIGS. 6E and 6F) and bone surface osteocalcin+ osteoblasts (FIG. 6G and FIG. 6H) in the same region were also observed in the iKO mice. We examined whether osteoblastic new bone formation was affected by deletion of Ezh2 in nestin+ cells. Goldner's Trichrome staining showed significantly decreased newly formed bone in the primary spongiosa region in the Ezh2 iKO mice compared with the WT mice (FIG. 6I). The results suggest that Ezh2 functions to maintain the proliferative capacity of nestin+ cells in primary spongiosa of long bone during the postnatal and early pubertal periods, and Ezh2 downregulation or deficiency during this period leads to rapid senescence of the cells and subsequent loss of blood vessel formation and new bone formation in this rapid bone growth phase.

Epidemiologic studies suggest that 60% of the risk for osteoporosis can be explained by the bone mineral acquired by early adulthood, and peak bone mass in childhood is associated with bone mass and fracture risk later in life (Cooper and Melton, 1992; Farr and Khosla, 2015). We tested whether the reduced osteoblastic bone formation in mice induced by Ezh2 deficiency during early puberty results in bone deficit during adulthood. We administered 3 doses of tamoxifen to 3-week-old WT and Ezh2 iKO mice. The mice were killed at 16 weeks of age. Body weight and femoral length were not decreased in male or female Ezh2 iKO mice compared with WT controls at 16 weeks of age (FIG. S6A-S6D). Femora were harvested from 16-week-mice, and bone architecture of the femoral bone was measured by μCT. A significant reduction in the mass of trabecular bone was observed in the Ezh2 iKO mice relative to WT mice (FIG. 6J). The Ezh2 iKO mice exhibited reduced trabecular bone volume and number and greater trabecular bone separation compared with WT littermates (FIG. 6K-6N). No significant differences were observed for the cortical bone parameters including bone area, bone area/total area, and cortical bone thickness in the Ezh2 iKO mice as compared to their WT littermates (FIG. 6O-6R). Therefore, premature cellular senescence in primary spongiosa caused by Ezh2 deficiency during the prepubertal or early pubertal phase may be a key factor leading to osteoporosis in later life.

Example 6

Blood Vessels in Femoral Primary Spongiosa Undergo Senescence in Glucocorticoid-Treated Young Mice.

Figures 7A, 7B, 7C, 7D, 7E, 7F, 7G:
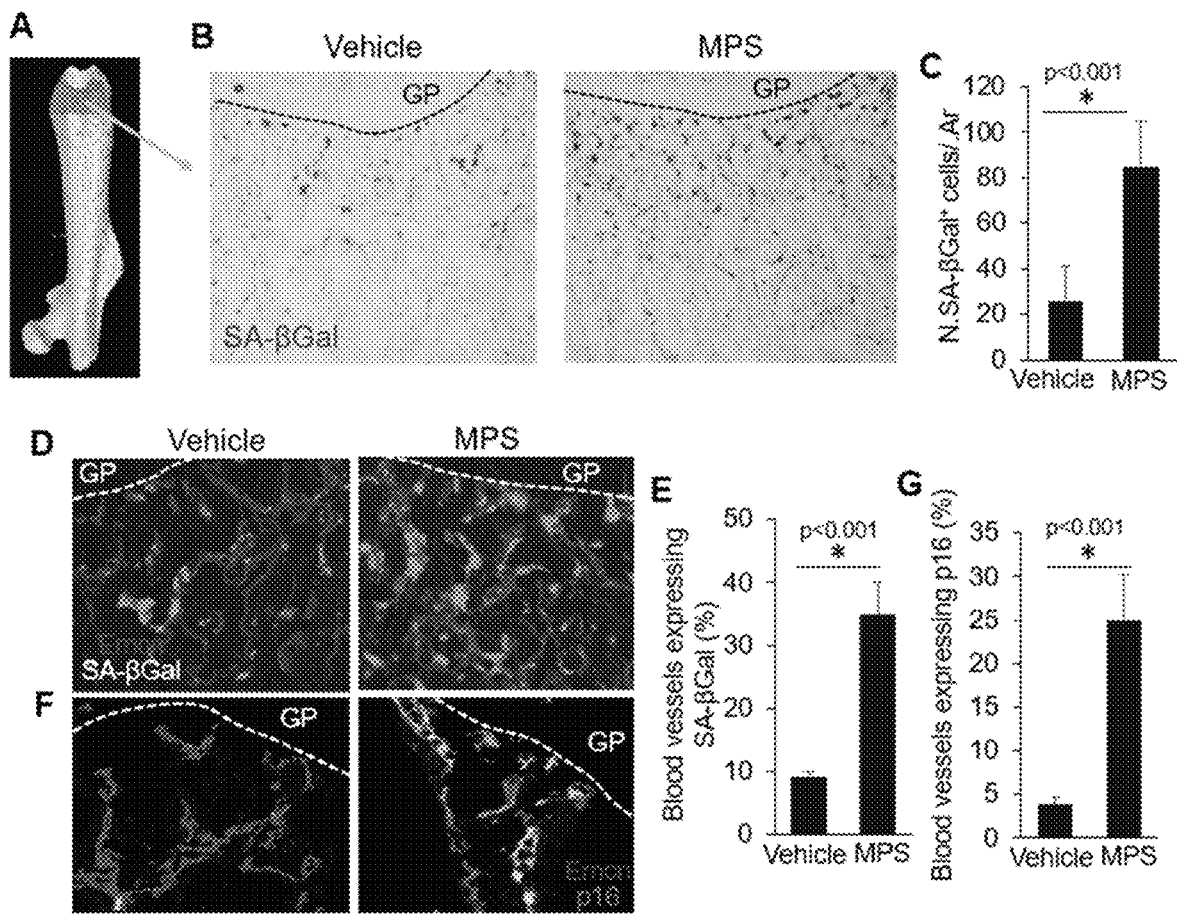
FIGS. 7A-7G. Blood vessels in femoral primary spongiosa undergo senescence in glucocorticoid-treated young mice. Four-week-old BALB/c mice were treated with methylprednisolone (MPS) or vehicle daily for 2 weeks. (7A and 7B) Representative senescence-associated β-galactosidase (SA-βGal) staining (blue) of SA-βGal+ cells in femoral metaphysis sections (7B). Numbers of SA-βGal+ cells per mm² tissue area in primary spongiosa (N. SA-βGal+ cells/Ar) (7C). (7D and 7E) SA-βGal staining (white) and Emcn immunofluorescence staining (red) in femoral metaphysis sections (7D). Quantification of the percentage of blood vessels that express SA-βGal (7E). (7F and 7G) Double-immunofluorescence images of femoral metaphysis sections using antibodies against p16 (green) and Emcn (red) (7F). DAPI stains nuclei blue. GP, growth plate. Quantification of the percentage of blood vessels that express p16 (7G). Five mice per group. Data are represented as mean±s.e.m.

Four-week-old BALB/c mice were treated with the glucocorticoid, methylprednisolone (MPS), or vehicle daily for 2 weeks. (FIGS. 7A and 7B) Quantitative analysis of relative fluorescence intensities in the primary spongiosa was performed. Representative senescence-associated β-galactosidase marker (SA-βGal) staining (blue) of SA-βGal+ cells in femoral metaphysis sections (7B). Increased numbers of SA-βGal+ cells per mm$^2$ tissue area in primary spongiosa were seen in MPS treated mice vs. control (N. SA-βGal+ cells/Ar) (7C). FIGS. 7D and 7E show increased SA-βGal staining (white) in Emcn+ blood vessel endothelial cells (red) in femoral metaphysis sections treated with MPS vs.

control. Quantification of the percentage of blood vessels that express SA-βGal (D). Double-immunofluorescence images of femoral metaphysis sections using antibodies against p16 (green) and Emcn (red) show significant increase in p16 staining in Emcn+ blood vessel endothelial cells in MPS treated mice vs. controls (FIGS. 7F, 7G).

Example 7

Increased Senescent Blood Vessel Endothelial Cells were Detected in Femoral Metaphysis in Glucocorticoid-Treated Young Mice.

Figures 8A, 8B, 8C, 8D, 8E, 8F, 8G:
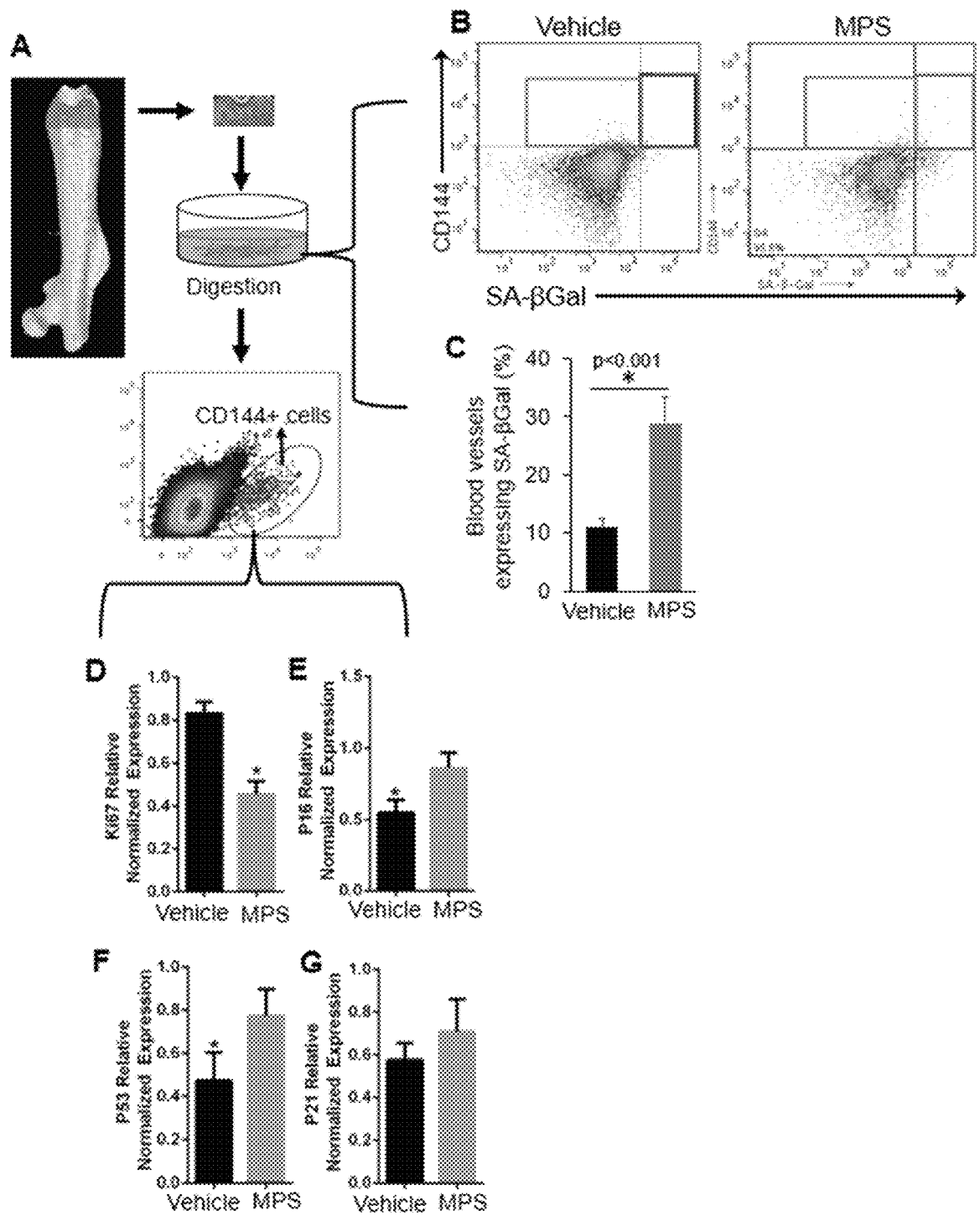
FIGS. 8A-8G. Increased senescent blood vessel endothelial cells were detected in femoral metaphysis in glucocorticoid-treated young mice. Four-week-old BALB/c mice were treated with methylprednisolone (MPS) or vehicle daily for 2 weeks. (8A) A schematic illustration of the steps to isolate CD144$^+$ vascular endothelial cells from femoral metaphyses. (8B-8C) Cells collected in (8A) were subjected to flow cytometry analysis of the SA-βGal expression in CD144+ cell population. (8D-8G) Quantitative RT-PCR analysis of ki67 (8D) p16$^{INK4a}$ (8E), p53 (8F), and p21$^{CIP1}$ (8G) expression in the sorted CD144$^+$ cells. n=3, Data are represented as mean±s.e.m. *p<0.01 as determined by Student's t-tests.

Four-week-old BALB/c mice were treated with methylprednisolone (MPS) or vehicle daily for 2 weeks. Blood vessel endothelial cells were isolated and digested. Cell sorting was performed to isolate the CD144+ vascular endothelial cells from the femoral metaphysis. Cells collected (FIG. 8A) were subjected to flow cytometry analysis of the SA-βGal expression in CD144+ cell population (FIG. 8B) Quantitative RT-PCR analysis was then performed on the sorted CD144+ cells to measure expression of ki67 (FIG. 8D), p16$^{INK4a}$ (FIG. 8E), p53 (FIG. 8F), and p21$^{CIP1}$ (FIG. 8G) compared to control mice. It was found that MPS treated mice had significantly more senescent blood vessel endothelial cells than control mice, and increased p16$^{INK4a}$, p21$^{CIP1}$, and p53 expression compared to controls. MPS treated mice had less ki67 expression compared to controls.

Example 8

Blood Vessels in Femoral Primary Spongiosa are Gradually Diminished in Glucocorticoid-Treated Young Mice.

Figures 9A, 9B, 9C, 9D:
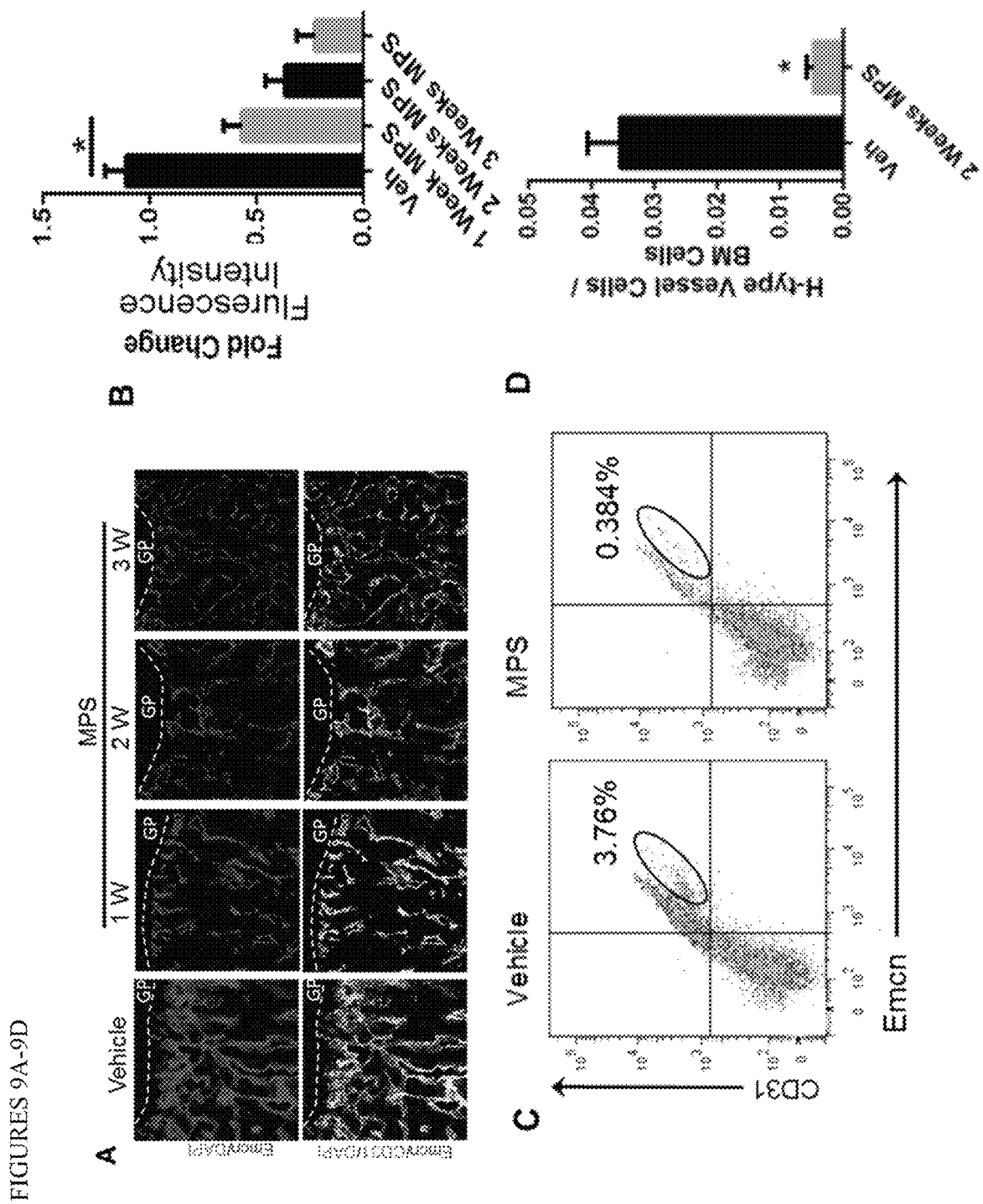
FIGS. 9A-9D. Blood vessels in femoral primary spongiosa are gradually diminished in glucocorticoid-treated young mice. Four-week-old BALB/c mice were treated with methylprednisolone (MPS) or vehicle daily for different time periods as indicated. (9A) Representative images of immunofluorescence staining of Emcn$^+$ cells (upper panel, red) and double-immunofluorescence of CD31$^+$ Emcn$^+$ cells (lower panel, yellow). DAPI stains nuclei blue. (9B) Quantitative analysis of Emcn$^+$ cells in femoral primary spongiosa. Representative images of flow cytometry analysis (9C) and the quantification of the percentage of the CD31$^+$ Emcn$^+$ cells isolated from femoral metaphysis (9D). n=5. Data are represented as mean±s.e.m. *p<0.01 as determined by Student's t-tests.

Four-week-old BALB/c mice were treated with methylprednisolone (MPS) or vehicle daily for different time periods as indicated. Cells were stained for Emcn and CD31+. FIG. 9A shows representative images of immunofluorescence staining of Emcn+ cells (upper panel, red) and double-immunofluorescence of CD31+ Emcn+ cells (lower panel, yellow). DAPI stains nuclei blue. Quantitative analysis of Emcn+ CD31+ cells in femoral primary spongiosa showed that blood vessels were decreased after MPS treatment in a time-dependent manner (FIG. 9B). Representative images of flow cytometry analysis (9C) and the quantification of the percentage of the CD31+Emcn+ cells isolated from femoral metaphysis (9D). The data showed that Emcn+ CD31+ H-type vessels were decreased after GC MPS treatment. n=5. Data are represented as mean±s.e.m. *$p<0.01$ as determined by Student's t-tests.

Example 10

GSK-J4 Treatment Restores Tail Length of Glucocorticoid-Treated Young Mice without Affecting Body Weight.

Figure 10A:
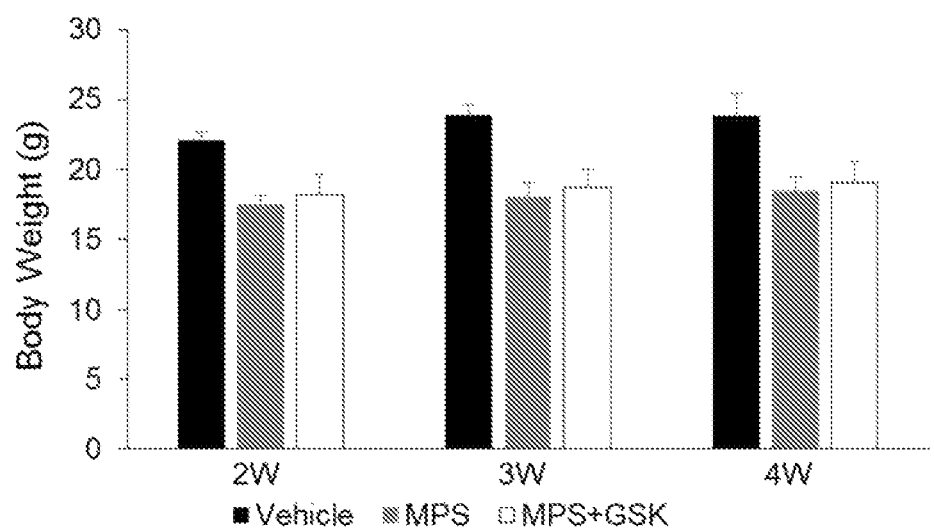
FIGS. 10A-10B. GSK-J4 treatment restores tail length of glucocorticoid-treated young mice without affecting body weight. Four-week-old BALB/c mice were treated with either methylprednisolone (MPS) alone or MPS plus GSK-J4 (10 mg/kg b.w.) daily. Body weight (10A) and Tail length (10B) were monitored at 2, 3, and 4 weeks after treatment.
Figure 10B:
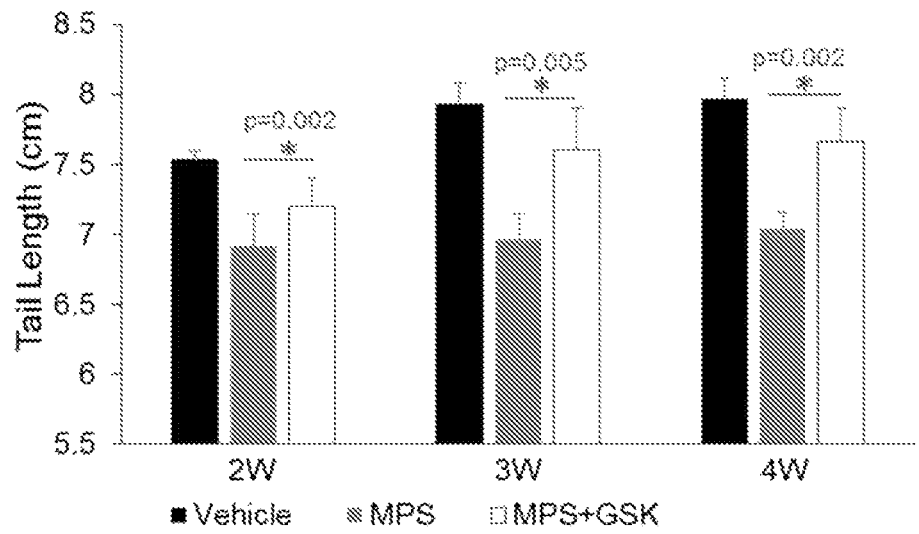

Four-week-old BALB/c mice were treated with either methylprednisolone (MPS) alone or MPS plus GSK-J4 (10 mg/kg b.w.) daily. Body weight (FIG. 10A) and Tail length (FIG. 10B) were monitored at 2, 3, and 4 weeks after treatment. The results show while there was no significant effect on the weight of the mice in any of the treatment groups (FIG. 10A), the treatment with MPS significantly shortened the tail length in the mice compared with controls, and the effect was abolished with concurrent treatment with GSK-J4 (FIG. 10B).

Example 10

GSK-J4 Treatment Rescues Bone Loss Phenotype Induced by Glucocorticoid in Young Mice.

Figures 11A, 11B, 11C, 11D, 11E, 11F:
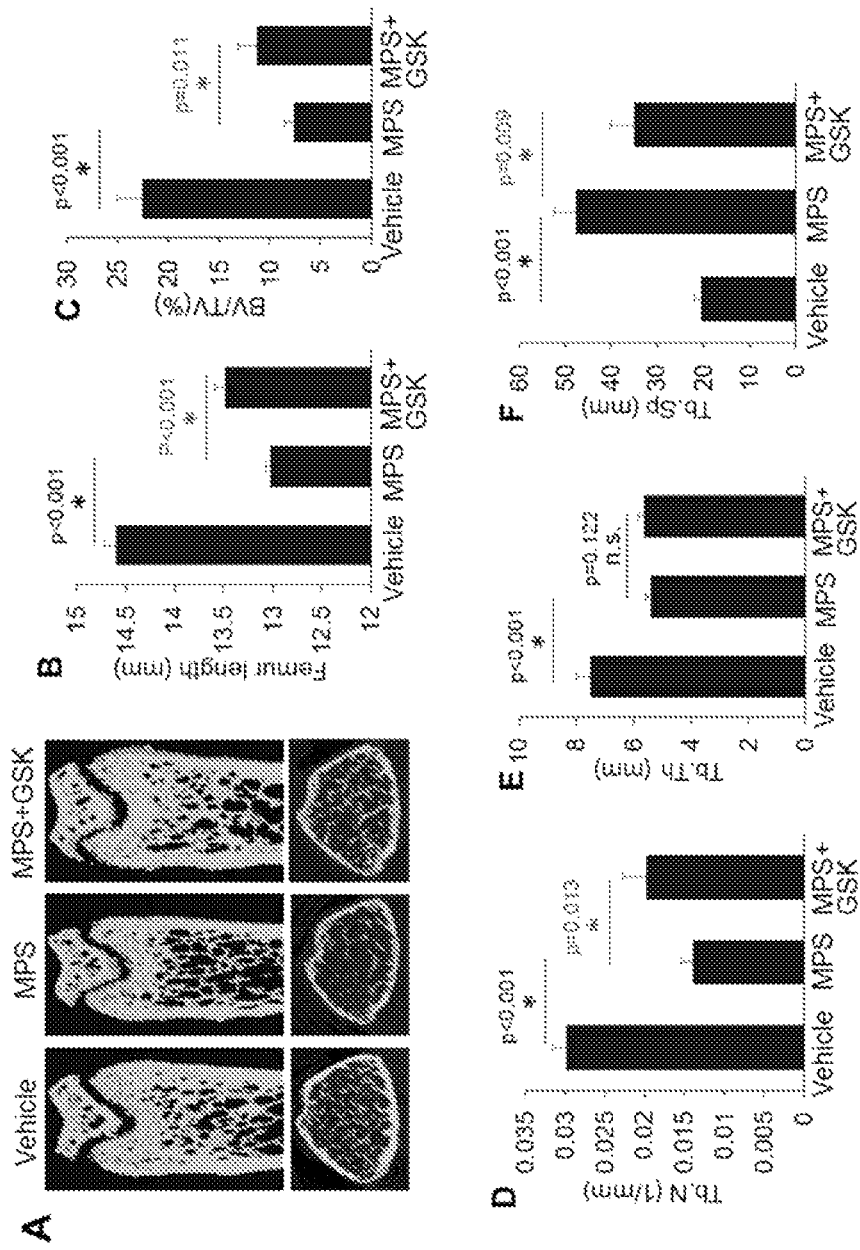
FIGS. 11A-11F. GSK-J4 treatment rescues bone loss phenotype induced by glucocorticoid in young mice. Four-week-old BALB/c mice were treated with either methylprednisolone (MPS) alone or MPS plus GSK-J4 (10 mg/kg b.w.) daily for 4 weeks. (11A) Representative μCT images of distal femur. Quantitative analyses of Femur length (11B), Trabecular bone volume fraction (BV/TV) (11C), trabecular number (Tb.N) (11D), trabecular thickness (Tb.Th) (11E), and trabecular separation (Tb.Sp) (11F). Seven mice per group; Data are represented as mean±s.e.m. *p<0.05 as determined by ANOVA.

Four-week-old BALB/c mice were treated with either methylprednisolone (MPS) alone or MPS plus GSK-J4 (10 mg/kg b.w.) daily for 4 weeks. μCT images of distal femur of each group was taken (FIG. 11A) and then measured for femur length (FIG. 11B). Quantitative analyses was also conducted on trabecular bone volume fraction (BV/TV) (FIG. 11C), trabecular number (Tb.N) (FIG. 11D), trabecular thickness (Tb.Th) (FIG. 11E), and trabecular separation (Tb.Sp) (FIG. 11F). The results show that treatment of the mice with GSK-J4 at least partially reversed the bone loss phenotype induced by MPS treatment.

Example 11

GSK-J4 Treatment Restores Angiogenesis and Osteogenesis Impaired by Glucocorticoid in Femoral Primary Spongiosa in Young Mice.

Figures 12A, 12B, 12C, 12D:
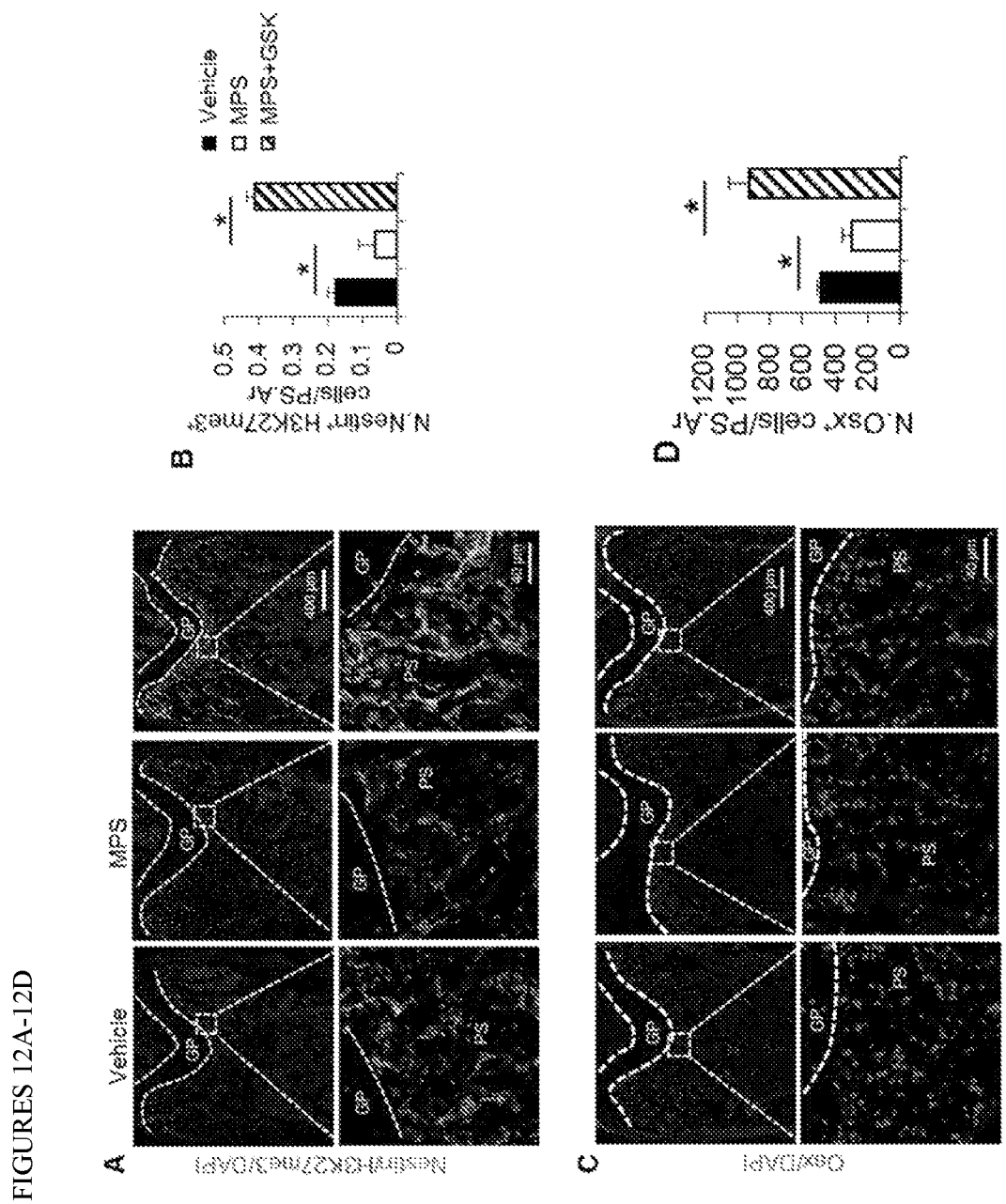
FIGS. 12A-12F. GSK-J4 treatment restores angiogenesis and osteogenesis impaired by glucocorticoid in femoral primary spongiosa in young mice. Four-week-old BALB/c mice were treated with either methylprednisolone (MPS) alone or MPS plus GSK-J4 (10 mg/kg b.w.) daily for 4 weeks. (12A-B) Double-immunofluorescence staining of femur sections was performed using antibodies against nestin (green) and H3K27me3 (red) (12A). Quantification of the percentage of nestin$^+$ cells that express H3K27me3 in the primary spongiosa (12B). Immunofluorescence staining of femur sections using antibody against osterix (Osx) (12C). Quantitative analysis of Osx$^+$ cells in the primary spongiosa (12D). Double-immunofluorescence staining of femur sections was performed using antibodies against CD31 (green) and endomucin (Emcn) (red) (12E). Quantitative analysis of relative fluorescence intensities in the primary spongiosa (12F). DAPI stains nuclei blue. Seven mice per group. GP, growth plate. PS, primary spongiosa.
Figure 12E:
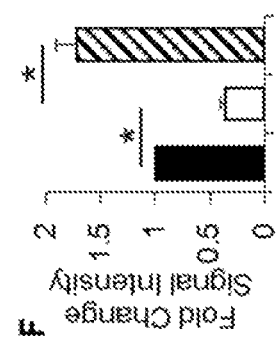
Figure 12F:
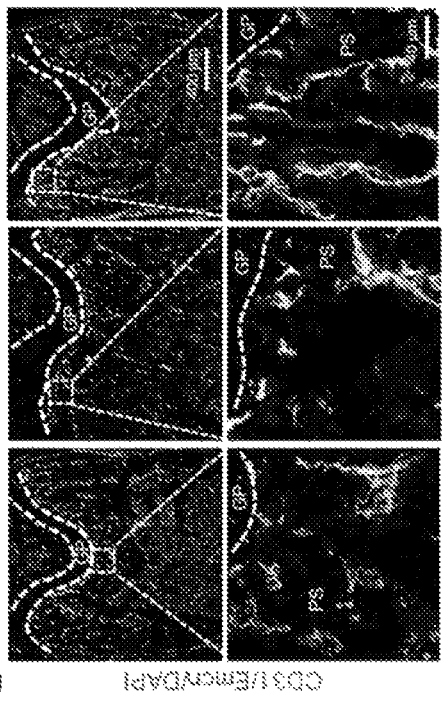

Four-week-old BALB/c mice were treated with either methylprednisolone (MPS) alone or MPS plus GSK-J4 (10 mg/kg b.w.) daily for 4 weeks. After treatment, the mice were sacrificed and double-immunofluorescence staining of femur sections was performed using antibodies against nestin (green) and H3K27me3 (red) (FIG. 12A) and quantified as the percentage of nestin$^+$ cells that express H3K27me3 in the primary spongiosa (FIG. 12B). Femur sections were stained for immunofluorescence detection using antibody against osterix (Osx) (FIG. 12C), and quantified for the amount of Osx$^+$ cells in the primary spongiosa (FIG. 12D). Double-immunofluorescence staining of femur sections was also performed using antibodies against CD31 (green) and endomucin (Emcn) (red) (FIG. 12E), and the relative fluorescence intensities in the primary spongiosa of each were quantified (FIG. 12F). The results show that treatment with GSK-J4 greatly improve angiogenesis and osteogenesis compared to both MPS treatment alone and when compared to controls as well.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

Adam, R. C., and Fuchs, E. (2016). The Yin and Yang of Chromatin Dynamics In Stem Cell Fate Selection. Trends in Genetics 32, 89-100.

Adam, R. C., Yang, H., Rockowitz, S., Larsen, S. B., Nikolova, M., Oristian, D. S., Polak, L., Kadaja, M., Asare, A., and Zheng, D. (2015). Pioneer factors govern super-enhancer dynamics in stem cell plasticity and lineage choice. Nature 521, 366-370.

Anai, M. (2011). Activation of Bmp2-Smad1 signal and its regulation by coordinated alteration of H3K27 trimethylation in Ras-induced senescence. Plos Genetics 7, 749-771.

Bailey, D., McKay, H., Mirwald, R., Crocker, P., and Faulkner, R. (1999). A six-year longitudinalstudy of the relationship of physical activity to bone mineral accrual in growing children: the University of Saskatchewan Bone Mineral Accrual Study. Journal of Bone and Mineral Research 14, 1672-1679.

Baker, D. J., Childs, B. G., Durik, M., Wijers, M. E., Sieben, C. J., Zho ng, J., Saltness, R. A., Jeganathan, K. B., Verzosa, G. C., Pezeshki, A., et al. (2016). Naturally occurring p16(Ink4a)-positive cells shorten healthy lifespan. Nature 530, 184-189.

Baker, D. J., Wijshake, T., Tchkonia, T., LeBrasseur, N. K., Childs, B. G., van de Sluis, B., Kirkland, J. L., and van Deursen, J. M. (2011). Clearance of p16Ink4a-positive senescent cells delays ageing-associated disorders. Nature 479, 232-236.

Bernstein, B. E., Mikkelsen, T. S., Xie, X., Kamal, M., Huebert, D. J., Cuff, J., Fry, B., Meissner, A., Wernig, M., and Plath, K. (2006). A bivalent chromatin structure marks key developmental genes in embryonic stem cells. Cell 125, 315-326.

Cakouros, D., Isenmann, S., Cooper, L., Zannettino, A., Anderson, P., Glackin, C., and Gronthos, S. (2012). Twist-1 induces Ezh2 recruitment regulating histone methylation along the Ink4A/Arf locus in mesenchymal stem cells. Molecular and cellular biology 32, 1433-1441.

Callewaert, F., Venken, K., Kopchick, J. J., Torcasio, A., van Lenthe, G. H., Boonen, S., and Vanderschueren, D. (2010). Sexual dimorphism in cortical bone size and strength but not density is determined by independent and time-specific actions of sex steroids and IGF-1: evidence from pubertal mouse models. Journal of bone and mineral research: the official journal of the American Society for Bone and Mineral Research 25, 617-626.

Chen, Y. H., Chung, C. C., Liu, Y. C., Yeh, S. P., Hsu, J. L., Hung, M. C., Su, H. L., and Li, L. Y. (2016). Enhancer of Zeste Homolog 2 and Histone Deacetylase 9c Regulate Age-Dependent Mesenchymal Stem Cell Differentiation into Osteoblasts and Adipocytes. Stem cells 34, 2183-2193.

Cheung, M. C., Spalding, P. B., Gutierrez, J. C., Balkan, W., Namias, N., Koniaris, L. G., and Zimmers, T. A. (2008). Body surface area prediction in normal, hypermuscular, and obese mice. Journal of Surgical Research 153, 326-331.

Cooper, C., and Melton, L. J. (1992). Epidemiology of osteoporosis. Trends in Endocrinology & Metabolism 3, 224-229.

Decker, R. S., Koyama, E., Enomotoiwamoto, M., Maye, P., Rowe, D., Zhu, S., Schultz, P. G., and Pacifici, M. (2014). Mouse limb skeletal growth and synovial joint development are coordinately enhanced by Kartogenin. Developmental biology 395, 255-267.

Delacour, A., Nepote, V., Trumpp, A., and Herrera, P. L. (2004). Nestin expression in pancreatic exocrine cell lineages. Mechanisms of Development 121, 3-14.

Demaria, M., Ohtani, N., Youssef, S. A., Rodier, F., Toussaint, W., Mitchell, J. R., Laberge, R.-M., Vijg, J., Van Steeg, H., and Dollé, M. E. (2014). An essential role for senescent cells in optimal wound healing through secretion of PDGF-AA. Dev Cell 31, 722-733.

Dudakovic, A., Camilleri, E. T., Riester, S. M., Paradise, C. R., Gluscevic, M., O'Toole, T. M., Thaler, R., Evans, J. M., Yan, H., Subramaniam, M., et al. (2016). Enhancer of Zeste Homolog 2 Inhibition Stimulates Bone Formation and Mitigates Bone Loss Caused by Ovariectomy in Skeletally Mature Mice. The Journal of Biological Chemistry 291, 24594-24606.

Farr, J. N., and Khosla, S. (2015). Skeletal changes through the lifespan—from growth to senescence. Nat Rev Endocrinol 11, 513-521.

Gerber, H.-P., Vu, T. H., Ryan, A. M., Kowalski, J., Werb, Z., and Ferrara, N. (1999). VEGF couples hypertrophic cartilage remodeling, ossification and angiogenesis during endochondral bone formation. Nature medicine 5, 623-628.

Heaney, R., Abrams, S., Dawson-Hughes, B., Looker, A., Looker, A., Marcus, R., Matkovic, V., and Weaver, C. (2000). Peak bone mass. Osteoporosis international 11, 985-1009.

Hemming, S., Cakouros, D., Isenmann, S., Cooper, L., Menicanin, D., Zannettino, A., and Gronthos, S. (2014). EZH2 and KDM6A act as an epigenetic switch to regulate mesenchymal stem cell lineage specification. Stem cells 32, 802-815.

Hemming, S., Cakouros, D., Vandyke, K., Davis, M. J., Zannettino, A. C., and Gronthos, S. (2016). Identification of Novel EZH2 Targets Regulating Osteogenic Differentiation in Mesenchymal Stem Cells. Stem cells and development 25, 909-921.

Hernandez, C., Beaupre, G., and Carter, D. (2003). A theoretical analysis of the relative influences of peak BMD, age-related bone loss and menopause on the development of osteoporosis. Osteoporosis international 14, 843-847.

Hu, W., Lu, H., Wang, S., Yin, W., Liu, X., Dong, L., Chiu, R., Shen, L., Lu, W.-J., and Lan, F. (2016). Suppression of Nestin reveals a critical role for p38-EGFR pathway in neural progenitor cell proliferation. Oncotarget.

Isern, J., García-García, A., Martín, A. M., Arranz, L., Martín-Pérez, D., Torroja, C., Sánchez-Cabo, F., and Méndez-Ferrer, S. (2014). The neural crest is a source of mesenchymal stem cells with specialized hematopoietic stem cell niche function. Elife 3, e03696.

Itkin, T., Gur-Cohen, S., Spencer, J. A., Schajnovitz, A., Ramasamy, S. K., Kusumbe, A. P., Ledergor, G., Jung, Y., Milo, I., Poulos, M. G., et al. (2016). Distinct bone marrow blood vessels differentially regulate haematopoiesis. Nature 532, 323-328.

Janzen, V., Forkert, R., Fleming, H. E., Saito, Y., Waring, M. T., Dombkowski, D. M., Cheng, T., DePinho, R. A., Sharpless, N. E., and Scadden, D. T. (2006). Stem-cell ageing modified by the cyclin-dependent kinase inhibitor p16INK4a. Nature 443, 421-426.

Jing, H., Liao, L., An, Y., Su, X., Liu, S., Shuai, Y., Zhang, X., and Jin, Y. (2016). Suppression of EZH2 Prevents the Shift of Osteoporotic MSC Fate to Adipocyte and Enhances Bone Formation During Osteoporosis. Mol Ther 24, 217-229.

Juan, A. H., Derfoul, A., Feng, X., Ryall, J. G., Dell'Orso, S., Pasut, A., Zare, H., Simone, J. M., Rudnicki, M. A., and Sartorelli, V. (2011). Polycomb EZH2 controls self-renewal and safeguards the transcriptional identity of skeletal muscle stem cells. Genes & development 25, 789-794.

Juan, A. H., Wang, S., Ko, K. D., Zare, H., Tsai, P. F., Feng, X., Vivanco, K. O., Ascoli, A. M., Gutierrez-Cruz, G., Krebs, J., et al. (2016). Roles of H3K27me2 and H3K27me3 Examined during Fate Specification of Embryonic Stem Cells. Cell Rep 17, 1369-1382.

Kachinsky, A. M., Dominov, J. A., and Miller, J. B. (1994). Myogenesis and the intermediate filament protein, nestin. Developmental biology 165, 216-228.

Kamminga, L. M., Bystrykh, L. V., de Boer, A., Houwer, S., Douma, J., Weersing, E., Dontje, B., and de Haan, G. (2006). The Polycomb group gene Ezh2 prevents hematopoietic stem cell exhaustion. Blood 107, 2170-2179.

Kristensen, E., Hallgrimsson, B., Morck, D. W., and Boyd, S. K. (2010). Timing of growth hormone treatment affects trabecular bone microarchitecture and mineralization in growth hormone deficient mice. Bone 47, 295-300.

Kronenberg, H. M. (2003). Developmental regulation of the growth plate. Nature 423, 332-336. Kuilman, T., Michaloglou, C., Mooi, W. J., and Peeper, D. S. (2010). The essence of senescence. Genes & development 24, 2463-2479.

Kusumbe, A. P., Ramasamy, S. K., and Adams, R. H. (2014). Coupling of angiogenesis and osteogenesis by a specific vessel subtype in bone. Nature 507, 323-328.

Kusumbe, A. P., Ramasamy, S. K., Itkin, T., Mäe, M. A., Langen, U. H., Betsholtz, C., Lapidot, T., and Adams, R. H. (2016). Age-dependent modulation of vascular niches for haematopoietic stem cells. Nature.

Kusumbe, A. P., Ramasamy, S. K., Starsichova, A., and Adams, R. H. (2015). Sample preparation for high-resolution 3D confocal imaging of mouse skeletal tissue. Nature protocols 10, 1904-1914.

Lee, B. Y., Han, J. A., Im, J. S., Morrone, A., Johung, K., Goodwin, E. C., Kleijer, W. J., DiMaio, D., and Hwang, E. S. (2006). Senescence-associated β-galactosidase is lysosomal β-galactosidase. Aging cell 5, 187-195.

Li, C., Zhen, G., Chai, Y., Xie, L., Crane, J. L., Farber, E., Farber, C. R., Luo, X., Gao, P., Cao, X., et al. (2016). RhoA determines lineage fate of mesenchymal stem cells by modulating CTGF-VEGF complex in extracellular matrix. Nat Commun 7, 11455.

Liu, Z., Cao, W., Xu, L., Chen, X., Zhan, Y., Yang, Q., Liu, S., Chen, P., Jiang, Y., Sun, X., et al. (2015). The histone H3 lysine-27 demethylase Jmjd3 plays a critical role in specific regulation of Th17 cell differentiation. J Mol Cell Biol 7, 505-516.

Lui, J. C., Nilsson, O., and Baron, J. (2011). Growth plate senescence and catch-up growth. In Cartilage and Bone Development and Its Disorders (Karger Publishers), pp. 23-29.

Méndez-Ferrer, S., Michurina, T. V., Ferraro, F., Mazloom, A. R., Macarthur, B. D., Lira, S. A., Scadden, D. T., Ma'Ayan, A., Enikolopov, G. N., and Frenette, P. S. (2010). Mesenchymal and haematopoietic stem cells form a unique bone marrow niche. Nature 466, 829-834.

Manolides, A. S., and Cullen DMAkhter, M. P. (2010). Effects of glucocorticoid treatment on bone strength. Journal of bone and mineral metabolism 28, 532-539.

Mokrý, J., and Nemecek, S. (1998). Angiogenesis of extra- and intraembryonic blood vessels is associated with expression of nestin in endothelial cells. Folia Biologica 44, 155-161.

Molofsky, A. V., Slutsky, S. G., Joseph, N. M., He, S., Pardal, R., Krishnamurthy, J., Sharpless, N. E., and Morrison, S. J. (2006). Increasing p16INK4a expression decreases forebrain progenitors and neurogenesis during ageing. Nature 443, 448-452.

Muñoz-Espín, D., Cañamero, M., Maraver, A., Gómez-López, G., Contreras, J., Murillo-Cuesta, S., Rodriguez-Baeza, A., Varela-Nieto, I., Ruberte, J., and Collado, M. (2013). Programmed cell senescence during mammalian embryonic development. Cell 155, 1104-1118.

Mundy, C., Bello, A., Sgariglia, F., Koyama, E., and Pacifici, M. (2016). HhAntag, a Hedgehog Signaling Antagonist, Suppresses Chondrogenesis and Modulates Canonical and Non-Canonical BMP Signaling. Journal of Cellular Physiology 231, 1033.

Nilsson, O., and Baron, J. (2004). Fundamental limits on longitudinal bone growth: growth plate senescence and epiphyseal fusion. Trends in Endocrinology & Metabolism 15, 370-374.

Ono, N., and Kronenberg, H. M. (2015). Mesenchymal Progenitor Cells for the Osteogenic Lineage. Current molecular biology reports 1, 95-100.

Ono, N., Ono, W., Mizoguchi, T., Nagasawa, T., Frenette, P. S., and Kronenberg, H. M. (2014a). Vasculature-associated cells expressing nestin in developing bones encompass early cells in the osteoblast and endothelial lineage. Dev Cell 29, 330-339.

Ono, N., Ono, W., Nagasawa, T., and Kronenberg, H. M. (2014b). A subset of chondrogenic cells provides early mesenchymal progenitors in growing bones. Nature cell biology 16, 1157-1167.

Park, D., Xiang, A. P., Mao, F. F., Zhang, L., Di, C. G., Liu, X. M., Shao, Y., Ma, B. F., Lee, J. H., and Ha, K. S. (2010). Nestin is required for the proper self-renewal of neural stem cells. Stem cells 28, 2162-2171.

Ramasamy, S. K., Kusumbe, A. P., Wang, L., and Adams, R. H. (2014). Endothelial Notch activity promotes angiogenesis and osteogenesis in bone. Nature 507, 376-380.

Rauch, F. (2012). The dynamics of bone structure development during pubertal growth. J Musculoskelet Neuronal Interact 12, 1-6.

Riggs, B. L., Khosla, S., and Melton, L. J. (1999). The assembly of the adult skeleton during growth and maturation: implications for senile osteoporosis. The Journal of clinical investigation 104, 671-672.

Rizzoli, R., Bianchi, M. L., Garabedian, M., McKay, H. A., and Moreno, L. A. (2010). Maximizing bone mineral mass gain during growth for the prevention of fractures in the adolescents and the elderly. Bone 46, 294-305.

Rizzoli, R., and Biver, E. (2015). Glucocorticoid-induced osteoporosis: who to treat with what agent? Nat Rev Rheumatol 11, 98-109.

Rosen, C. J. (2000). The Epidemiology and Pathogenesis of Osteoporosis.

Sahlgren, C. M., Mikhailov, A., Vaittinen, S., Pallari, H. M., Kalimo, H., Pant, H. C., and Eriksson, J. E. (2003). Cdk5 Regulates the Organization of Nestin and Its Association with p35. Molecular & Cellular Biology 23, 5090-5106.

Sahlgren, C. M., Pallari, H. M., He, T., Chou, Y. H., Goldman, R. D., and Eriksson, J. E. (2006). A nestin scaffold links Cdk5/p35 signaling to oxidant-induced cell death. Embo J 25, 4808-4819.

Schellenberg, A., Lin, Q., Schüler, H., Koch, C. M., Joussen, S., Denecke, B., Walenda, G., Pallua, N., Suschek, C. V., and Zenke, M. (2011). Replicative senescence of mesenchymal stem cells causes DNA-methylation changes which correlate with repressive histone marks. Aging (Albany N.Y.) 3, 873-888.

Serrano, M. (2014). Senescence helps regeneration. Dev Cell 31, 671-672.

Siclari, V. A., Zhu, J., Akiyama, K., Liu, F., Zhang, X., Chandra, A., Nah, H.-D., Shi, S., and Qin, L. (2013). Mesenchymal progenitors residing close to the bone surface are functionally distinct from those in the central bone marrow. Bone 53, 575-586.

Storer, M., Mas, A., Robert-Moreno, A., Pecoraro, M., Ortells, M. C., Di Giacomo, V., Yosef, R., Pilpel, N., Krizhanovsky, V., and Sharpe, J. (2013). Senescence is a developmental mechanism that contributes to embryonic growth and patterning. Cell 155, 1119-1130.

Sun, X. Y., and An, J. (2004). Expression of nestin, an intermediate filament protein, in human fetal hepatic stem cells. Di 1 junyi da, xue xue bao; Academic journal of the first medical college of PLA 24, 207-209.

Tominaga, K. (2015). The emerging role of senescent cells in tissue homeostasis and pathophysiology. Pathobiology of Aging & Age-Related Diseases 5.

Triana-Martínez, F., Pedraza-Vázquez, G., Maciel-Barón, L., and Königsberg, M. (2016). Reflections on the role of senescence during development and aging. Archives of biochemistry and biophysics 598, 40-49.

Trowbridge, J. J., Snow, J. W., Kim, J., and Orkin, S. H. (2009). DNA methyltransferase 1 is essential for and uniquely regulates hematopoietic stem and progenitor cells. Cell stem cell 5, 442-449.

Tsai, C.-C., Su, P.-F., Huang, Y.-F., Yew, T.-L., and Hung, S.-C. (2012). Oct4 and Nanog directly regulate Dnmt1 to maintain self-renewal and undifferentiated state in mesenchymal stem cells. Molecular cell 47, 169-182.

van Deursen, J. M. (2014). The role of senescent cells in ageing. Nature 509, 439-446.

Veldhuis-Vlug, A. G., and Rosen, C. J. (2016). Mechanisms of marrow adiposity and its implications for skeletal health. Metabolism-clinical & Experimental 67, 106-114.

Wang, B., Jin, H., Shu, B., Mira, R. R., and Chen, D. (2015a). Chondrocytes-Specific Expression of Osteoprotegerin Modulates Osteoclast Formation in Metaphyseal Bone. 5, 13667.

Wang, Y., Menendez, A., Fong, C., Elalieh, H. Z., Kubota, T., Long, R., and Bikle, D. D. (2015b). IGF-I Signaling in Osterix-Expressing Cells Regulates Secondary Ossification Center Formation, Growth Plate Maturation, and Metaphyseal Formation during Postnatal Bone Development. Journal of Bone and Mineral Research 116, 422-429.

Wei, Y., Chen, Y. H., Li, L. Y., Lang, J., Yeh, S. P., Shi, B., Yang, C. C., Yang, J. Y., Lin, C. Y., Lai, C. C., et al. (2011). CDK1-dependent phosphorylation of EZH2 suppresses methylation of H3K27 and promotes osteogenic differentiation of human mesenchymal stem cells. Nat Cell Biol 13, 87-94.

Wiley, C. D., Velarde, M. C., Lecot, P., Liu, S., Sarnoski, E. A., Freund, A., Shirakawa, K., Lim, H. W., Davis, S. S., and Ramanathan, A. (2016). Mitochondrial dysfunction induces senescence with a distinct secretory phenotype. Cell metabolism 23, 303-314.

Wu, S., Yang, W., and De Luca, F. (2015). Insulin-Like Growth Factor-Independent Effects of Growth Hormone on Growth Plate Chondrogenesis and Longitudinal Bone Growth. Endocrinology 156, 2541-2551.

Xie, H., Cui, Z., Wang, L., Xia, Z., Hu, Y., Xian, L., Li, C., Xie, L., Crane, J., Wan, M., et al. (2014). PDGF-BB secreted by preosteoclasts induces angiogenesis during coupling with osteogenesis. Nature medicine 20, 1270-1278.

Yakar, S., and Isaksson, O. (2016). Regulation of skeletal growth and mineral acquisition by the GH/IGF-1 axis: lessons from mouse models. Growth Hormone & IGF Research 28, 26-42.

Ye, L., Fan, Z., Yu, B., Chang, J., Al Hezaimi, K., Zhou, X., Park, N. H., and Wang, C. Y. (2012). Histone demethylases KDM4B and KDM6B promotes osteogenic differentiation of human MSCs. Cell stem cell 11, 50-61.

Yue, R., Zhou, B. O., Shimada, I. S., Zhao, Z., and Morrison, S. J. (2016). Leptin Receptor Promotes Adipogenesis and Reduces Osteogenesis by Regulating Mesenchymal Stromal Cells in Adult Bone Marrow. Cell stem cell 18, 782-796.

Zhou, B. O., Yue, R., Murphy, M. M., Peyer, J. G., and Morrison, S. J. (2014). Leptin-receptor expressing mesenchymal stromal cells represent the main source of bone formed by adult bone marrow. Cell stem cell 15, 154-168.

What is claimed is:

1. A method for treating one or more of:
the cessation of bone/growth or accrual in a pediatric or juvenile subject,
primary osteoporosis in a pediatric or juvenile subject,
osteoporosis in a pediatric or juvenile subject,
secondary osteoporosis in a pediatric or juvenile, and
comprising administering to the subject an effective amount of N-[2-(2-Pyridinyl)-6-(1,2,4,5-tetrahydro-3H-3-benzazepin-3-yl)-4-pyrimidinyl]-β-alanine ethyl ester, and tautomers, isomers, enantiomers, stereoisomers, and diastereoisomers, and the pharmaceutically-acceptable salts thereof.

2. The method of claim 1, wherein the pediatric or juvenile subject is suffering from osteogenesis imperfecta (OI).

3. The method of claim 1, wherein the juvenile or young adult subject is suffering from rheumatoid disorders, Crohn's disease, nephrotic syndrome, juvenile idiopathic arthritis, glomerulonephritis, Graves' disease, Guillain-Barré syndrome, idiopathic thrombocytopenic purpura, myasthenia gravis, myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, thyroiditis, uveitis, vitiligo, and granulomatosis with polyangiitis (Wegener's).

4. The method of claim 1, wherein the juvenile or young adult subject is suffering from disorders which compromise normal weight-bearing and mobility, cerebral palsy, Rett syndrome, Duchenne muscular dystrophy, spina bifida, and spinal muscular atrophy.

5. The method of claim 1, wherein the effective amount of the N-[2-(2-Pyridinyl)-6-(1,2,4,5-tetrahydro-3H-3-benzazepin-3-yl)-4-pyrimidinyl]-β-alanine ethyl ester, and tautomers, isomers, enantiomers, stereoisomers, and diastereoisomers, and the pharmaceutically-acceptable salts thereof is administered at a concentration of about 100 ng/Kg to about 1000 mg/Kg.

6. The method of claim 5, wherein the concentration of the effective amount of the N-[2-(2-Pyridinyl)-6-(1,2,4,5-tetrahydro-3H-3-benzazepin-3-yl)-4-pyrimidinyl]-β-alanine ethyl ester, and tautomers, isomers, enantiomers, stereoisomers, and diastereoisomers, and the pharmaceutically-acceptable salts thereof administered is about 100 mg/Kg.

* * * * *

UNITED STATES PATENT AND TRADEMARK OFFICE
CERTIFICATE OF CORRECTION

PATENT NO. : 11,524,011 B2
APPLICATION NO. : 16/643672
DATED : December 13, 2022
INVENTOR(S) : Mei Wan and Xu Cao It is certified that error appears in the above-identified patent and that said Letters Patent is hereby corrected as shown below:

In the Claims

Column 45, Claim 1, Line 36 reads:
comprising administering to the subject an effective Whereas it should read:
short stature in a pediatric or juvenile subject,
comprising administering to the subject an effective Signed and Sealed this
Seventeenth Day of January, 2023

Katherine Kelly Vidal
*Director of the United States Patent and Trademark Office*

SEQUENCE LISTING

<160> NUMBER OF SEQ ID NOS: 30

<210> SEQ ID NO 1
<211> LENGTH: 24
<212> TYPE: DNA
<213> ORGANISM: artificial sequence
<220> FEATURE:
<223> OTHER INFORMATION: synthetic sequence

<400> SEQUENCE: 1
ctgcttggtc taatgctaac tgtg                                           24

<210> SEQ ID NO 2
<211> LENGTH: 24
<212> TYPE: DNA
<213> ORGANISM: Artificial Sequence
<220> FEATURE:
<223> OTHER INFORMATION: synthetic sequence

<400> SEQUENCE: 2
ggtctttatt tagctcaggc ctgc                                          24

<210> SEQ ID NO 3
<211> LENGTH: 24
<212> TYPE: DNA
<213> ORGANISM: Artificial Sequence
<220> FEATURE:
<223> OTHER INFORMATION: synthetic sequence

<400> SEQUENCE: 3
ggtctttatt tagctcaggc ctgc                                          24

<210> SEQ ID NO 4
<211> LENGTH: 20
<212> TYPE: DNA
<213> ORGANISM: Artificial Sequence
<220> FEATURE:
<223> OTHER INFORMATION: synthetic sequence

<400> SEQUENCE: 4
tccgatcctt tagcgctgtt                                               20

<210> SEQ ID NO 5
<211> LENGTH: 20
<212> TYPE: DNA
<213> ORGANISM: Artificial Sequence
<220> FEATURE:
<223> OTHER INFORMATION: synthetic sequence

<400> SEQUENCE: 5
acactctgct cctgacctgg                                               20

<210> SEQ ID NO 6
<211> LENGTH: 20
<212> TYPE: DNA
<213> ORGANISM: Artificial Sequence
<220> FEATURE:
<223> OTHER INFORMATION: synthetic sequence

<400> SEQUENCE: 6
acactctgct cctgacctgg                                               20

<210> SEQ ID NO 7
<211> LENGTH: 22
<212> TYPE: DNA
<213> ORGANISM: Artificial Sequence
<220> FEATURE:
<223> OTHER INFORMATION: synthetic sequence

<400> SEQUENCE: 7
ggagccaccc attaaactaa ct                                            22

<210> SEQ ID NO 8
<211> LENGTH: 24
<212> TYPE: DNA
<213> ORGANISM: Artificial Sequence
<220> FEATURE:
<223> OTHER INFORMATION: synthetic sequence

<400> SEQUENCE: 8
caaaaataag acactgaaaa ctcg                                              24

<210> SEQ ID NO 9
<211> LENGTH: 19
<212> TYPE: DNA
<213> ORGANISM: Artificial Sequence
<220> FEATURE:
<223> OTHER INFORMATION: synthetic sequence

<400> SEQUENCE: 9
caggaccaac ccactcctt                                                    19

<210> SEQ ID NO 10
<211> LENGTH: 20
<212> TYPE: DNA
<213> ORGANISM: Artificial Sequence
<220> FEATURE:
<223> OTHER INFORMATION: synthetic sequence

<400> SEQUENCE: 10
cacagttggt cagggacaga                                                   20

<210> SEQ ID NO 11
<211> LENGTH: 20
<212> TYPE: DNA
<213> ORGANISM: Artificial Sequence
<220> FEATURE:
<223> OTHER INFORMATION: synthetic sequence

<400> SEQUENCE: 11
ggctcccgtt agacactctc                                                   20

<210> SEQ ID NO 12
<211> LENGTH: 20
<212> TYPE: DNA
<213> ORGANISM: Artificial Sequence
<220> FEATURE:
<223> OTHER INFORMATION: synthetic sequence

<400> SEQUENCE: 12
ctggctctgc tccatttgac                                                   20

<210> SEQ ID NO 13
<211> LENGTH: 20
<212> TYPE: DNA
<213> ORGANISM: Artificial Sequence
<220> FEATURE:
<223> OTHER INFORMATION: synthetic sequence

<400> SEQUENCE: 13
actggtggag tggagtggac                                                   20

<210> SEQ ID NO 14
<211> LENGTH: 20
<212> TYPE: DNA
<213> ORGANISM: Artificial Sequence
<220> FEATURE:
<223> OTHER INFORMATION: synthetic sequence

<400> SEQUENCE: 14
ctggggtttg gaatgcctaa                                                   20

<210> SEQ ID NO 15
<211> LENGTH: 20

```
<212> TYPE: DNA
<213> ORGANISM: Artificial Sequence
<220> FEATURE:
<223> OTHER INFORMATION: synthetic sequence

<400> SEQUENCE: 15
cagtttatgg aaggccacct                                              20

<210> SEQ ID NO 16
<211> LENGTH: 20
<212> TYPE: DNA
<213> ORGANISM: Artificial Sequence
<220> FEATURE:
<223> OTHER INFORMATION: synthetic sequence

<400> SEQUENCE: 16
gtaactgctg cccaaaactga                                             20

<210> SEQ ID NO 17
<211> LENGTH: 19
<212> TYPE: DNA
<213> ORGANISM: Artificial Sequence
<220> FEATURE:
<223> OTHER INFORMATION: synthetic sequence

<400> SEQUENCE: 17
gaaagagttc ggggcgttg                                               19

<210> SEQ ID NO 18
<211> LENGTH: 21
<212> TYPE: DNA
<213> ORGANISM: Artificial Sequence
<220> FEATURE:
<223> OTHER INFORMATION: synthetic sequence

<400> SEQUENCE: 18
gagagccatc tggagcagca t                                            21

<210> SEQ ID NO 19
<211> LENGTH: 21
<212> TYPE: DNA
<213> ORGANISM: Artificial Sequence
<220> FEATURE:
<223> OTHER INFORMATION: synthetic sequence

<400> SEQUENCE: 19
agaaggtact tacggtgtgg t                                            21

<210> SEQ ID NO 20
<211> LENGTH: 22
<212> TYPE: DNA
<213> ORGANISM: Artificial Sequence
<220> FEATURE:
<223> OTHER INFORMATION: synthetic sequence

<400> SEQUENCE: 20
gagagatttc ccgaattgca gt                                           22

<210> SEQ ID NO 21
<211> LENGTH: 20
<212> TYPE: DNA
<213> ORGANISM: Artificial Sequence
<220> FEATURE:
<223> OTHER INFORMATION: synthetic sequence

<400> SEQUENCE: 21
```
atcgccttcg acatcatcgc                                                    20

<210> SEQ ID NO 22
<211> LENGTH: 20
<212> TYPE: DNA
<213> ORGANISM: Artificial Sequence
<220> FEATURE:
<223> OTHER INFORMATION: synthetic sequence

<400> SEQUENCE: 22
ccccatgcgt actccatgag                                                    20

<210> SEQ ID NO 23
<211> LENGTH: 22
<212> TYPE: DNA
<213> ORGANISM: Artificial Sequence
<220> FEATURE:
<223> OTHER INFORMATION: synthetic sequence

<400> SEQUENCE: 23
accgtggagt agtttatctg gg                                                 22

<210> SEQ ID NO 24
<211> LENGTH: 22
<212> TYPE: DNA
<213> ORGANISM: Artificial Sequence
<220> FEATURE:
<223> OTHER INFORMATION: synthetic sequence

<400> SEQUENCE: 24
tgtttccagt ccgcttactt ct                                                 22

<210> SEQ ID NO 25
<211> LENGTH: 21
<212> TYPE: DNA
<213> ORGANISM: Artificial Sequence
<220> FEATURE:
<223> OTHER INFORMATION: synthetic sequence

<400> SEQUENCE: 25
ccagactgcc agaatcgctt t                                                  21

<210> SEQ ID NO 26
<211> LENGTH: 19
<212> TYPE: DNA
<213> ORGANISM: Artificial Sequence
<220> FEATURE:
<223> OTHER INFORMATION: synthetic sequence

<400> SEQUENCE: 26
caggtgcttt ttgaggcca                                                     19

<210> SEQ ID NO 27
<211> LENGTH: 22
<212> TYPE: DNA
<213> ORGANISM: Artificial Sequence
<220> FEATURE:
<223> OTHER INFORMATION: synthetic sequence

<400> SEQUENCE: 27
agtgacttgg attttccagc ac                                                 22

<210> SEQ ID NO 28
<211> LENGTH: 21
<212> TYPE: DNA
<213> ORGANISM: Artificial Sequence

```
<220> FEATURE:
<223> OTHER INFORMATION: synthetic sequence

<400> SEQUENCE: 28
aattctgttg taagggcgac c                                        21

<210> SEQ ID NO 29
<211> LENGTH: 20
<212> TYPE: DNA
<213> ORGANISM: Artificial Sequence
<220> FEATURE:
<223> OTHER INFORMATION: synthetic sequence

<400> SEQUENCE: 29
cgggcggaca aaagaagaac                                          20

<210> SEQ ID NO 30
<211> LENGTH: 24
<212> TYPE: DNA
<213> ORGANISM: Artificial Sequence
<220> FEATURE:
<223> OTHER INFORMATION: synthetic sequence

<400> SEQUENCE: 30
catagacttg catcagatcc tcca                                     24
```